(12) United States Patent
Rolfs et al.

(10) Patent No.: US 11,204,357 B2
(45) Date of Patent: Dec. 21, 2021

(54) METHOD FOR THE DIAGNOSIS OF FARBER'S DISEASE

(71) Applicant: Centogene GmbH, Rostock (DE)

(72) Inventors: Arndt Rolfs, Berlin (DE); Claudia Cozma, Rostock (DE)

(73) Assignee: Centogene GmbH, Rostock (DE)

( * ) Notice: Subject to any disclaimer, the term of this patent is extended or adjusted under 35 U.S.C. 154(b) by 131 days.

(21) Appl. No.: 15/742,317

(22) PCT Filed: Jul. 8, 2016

(86) PCT No.: PCT/EP2016/001182
§ 371 (c)(1),
(2) Date: Jan. 5, 2018

(87) PCT Pub. No.: WO2017/005374
PCT Pub. Date: Jan. 12, 2017

(65) Prior Publication Data
US 2018/0203024 A1    Jul. 19, 2018

(30) Foreign Application Priority Data
Jul. 8, 2015   (EP) .................................... 15002041

(51) Int. Cl.
| | |
|---|---|
| *G01N 33/00* | (2006.01) |
| *G01N 33/92* | (2006.01) |
| *A61P 3/00* | (2006.01) |
| *A61K 48/00* | (2006.01) |
| *G01N 33/68* | (2006.01) |

(52) U.S. Cl.
CPC ........... *G01N 33/92* (2013.01); *A61K 48/005* (2013.01); *A61P 3/00* (2018.01); *G01N 33/6851* (2013.01); *G01N 33/6893* (2013.01); *C12Y 305/01023* (2013.01); *G01N 2405/00* (2013.01); *G01N 2800/04* (2013.01); *G01N 2800/52* (2013.01); *G01N 2800/60* (2013.01)

(58) Field of Classification Search
CPC .............. G01N 33/92; G01N 33/6893; G01N 33/6851; G01N 2405/00; G01N 2800/04; G01N 2800/52
See application file for complete search history.

(56) References Cited

U.S. PATENT DOCUMENTS

2010/0233680 A1*  9/2010  Taylor .................. C12Q 1/6886
                                                       435/6.14

OTHER PUBLICATIONS

Yoo, Hye Hyun et al. "Liquid chromatography-tandem mass spectrometric determination of ceramides and related lipid species in cellular extracts." Journal of Chromatography B (2006) 843 327-333 (Year: 2006).*
Cozma, Claudia et al. "C26-ceramide as highly sensitive biomarker for the diagnosis of Farber disease." Scientific Reports (2017) 7 6149. (Year: 2017).*
Guan, Xue Li et al. "Mass spectrometry-based profiling of phospholipids and sphingolipids in extracts from *Saccharomyces cerevisiae*." Yeast (2006) 23 465-477. (Year: 2006).*
Noe, Julie et al. "CFTR regulation of intracellular pH and ceramides is required for lung endothelial cell apoptosis." American Journal of Respiratory Cell and Molecular Biology (2009) 41 314-323. (Year: 2009).*
Dworski et al., "Altered MCP-1 and ceramide metabolite levels in serum from Farber mice and Farber patients," Molecular Genetics and Metabolism, vol. 111, No. 1, Feb. 1, 2014, Abstract, 1 page.
Jones et al., "On-tissue profiling of ceramides and other sphingolipids on lysosomal disorders using high resolution MALDI-imaging mass spectrometry," Molecular Genetics and Metabolism, vol. 111, No. 2, Feb. 1, 2014, Abstract, pp. S56-S57.
Li et al., "Dried blood spot sampling in combination with LC-MS/MS for quantitative analysis of small molecules," Biomedical Chromatography, vol. 24, No. 1, Jan. 1, 2010, pp. 49-65.
Ramsubir et al., "Enhancement of gene therapy approaches for the correction of farber disease," Molecular Therapy, Nature Publishing Group, GB, vol. 9, May 1, 2004, Abstract, p. S330.
Ramsubir et al., "In vivo delivery of human acid ceramidase via cord blood transplantation and direct injection of lentivirus as novel treatment approaches for Farber disease," Molecular Genetics and Metabolism, vol. 95, No. 3, Nov. 1, 2008, pp. 133-141.
Sugita et al., "High performance liquid chromatography of ceramides: application to analysis in human tissues and demonstration of ceramide excess in Farber's disease," Journal of Lipid Research, May 1, 1974, pp. 223-226.
Zhou et al., "Spinal Muscular Atrophy Associated with Progressive Myoclonic Epilepsy Is Caused by Mutations in ASAH1," American Journal of Human Genetics, vol. 91, No. 1, May 1, 2012, pp. 5-14.
International Search Report and Written Opinion, PCT/EP2016/001182, dated Sep. 23, 2016, 12 pages.
Yoo et al., "Liquid chromatography-tandem mass spectrometric determination of ceramides and related lipid species in cellular extracts," Journal of Chromatography B, 843 (2006), pp. 327-333.
First Office Action, Chinese Patent Application No. 201680039756.4, dated Apr. 26, 2021.

* cited by examiner

*Primary Examiner* — Christopher Adam Hixson
(74) *Attorney, Agent, or Firm* — Stanek Lemon Crouse & Meeks, PA

(57) ABSTRACT

The present invention is related to a method for diagnosing Farber's disease in a subject, wherein the method comprises detecting C26 ceramide in a sample from the subject.

4 Claims, 9 Drawing Sheets

METHOD FOR THE DIAGNOSIS OF FARBER'S DISEASE

CROSS-REFERENCE TO RELATED APPLICATIONS

This application is a 35 U.S.C. § 371 National Stage Entry of International Application No. PCT/EP2016/001182 having an international filing date of Jul. 8, 2016, which claims the benefit of European Application No. EP 15 002 041.0 filed Jul. 8, 2015, the contents of which are hereby incorporated herein by reference in their entireties.

The present invention is related to a method for diagnosing Farber's disease in a subject, a method for determining the course of Farber's disease in a subject, a method for determining the effectiveness of at least one treatment applied to a subject being positively tested for suffering from or being at risk of suffering from Farber's disease, a method for determining the effectiveness of a compound for the treatment of Farber's disease, a method for the treatment of Farber's disease, use of mass spectrometric analysis for the detection of a biomarker, use of a biomarker for the diagnosis of Farber's disease, use of an internal standard to quantify a biomarker present in a sample from the subject, and a kit for determining the presence of a biomarker in a sample from a subject.

BACKGROUND

Lysosomal storage diseases, also referred to herein as lysosomal storage disorders or LSDs, are a group of rare inherited metabolic disorders that result from defects in lysosomal function. LSDs result when a specific organelle in the body's cells—the lysosome—malfunctions. One of the lysosomal storage diseases is Farber's disease.

Farber's disease, which is also known as AC deficiency, acid ceramidase deficiency, acylsphingosine deacylase deficiency, ceramidase deficiency, Farber disease, Farber's lipogranulomatosis or Farber-Uzman syndrome, describes a group of inherited metabolic disorders called lipid storage diseases. In affected individuals, excess amounts of lipids such as oils, fatty acids, and related compounds, build up to harmful levels in the joints, tissues, and central nervous system. The liver, heart, and kidneys may also be affected.

Three classic signs occur in Farber' disease: a hoarse voice or a weak cry, small lumps of fat under the skin and in other tissues which are referred to as lipogranulomas, and swollen and painful joints. Symptoms are typically seen in the first few weeks of life and include impaired motor and mental ability and difficulty with swallowing. Other symptoms may include arthritis, swollen lymph nodes and joints, hoarseness, nodules under the skin and, sometimes, in the lungs and other parts of the body, chronic shortening of muscles or tendons around joints, and vomiting. Affected subjects may require the insertion of a breathing tube. In severe cases, the liver and spleen are enlarged.

Types of Farber's disease based on their characteristic features:
  Type 1 is the most common, or classical, form of this condition and is associated with the classic signs of voice, skin, and joint problems that begin a few months after birth. Developmental delay and lung disease also commonly occur. Infants born with type 1 Farber's disease usually survive only into early childhood.
  Types 2 and 3 generally have less severe signs and symptoms than the other types. Affected individuals have the three classic signs and usually do not have developmental delay. Children with these types of Farber's disease typically live into mid- to late childhood.
  Types 4 and 5 are associated with severe neurological problems. Type 4 usually causes life-threatening health problems beginning in infancy due to massive lipid deposits in the liver, spleen, lungs, and immune system tissues. Children with this type typically do not survive past their first year of life. Type 5 is characterized by progressive decline in brain and spinal cord (central nervous system) function, which causes paralysis of the arms and legs (quadriplegia), seizures, loss of speech, involuntary muscle jerks (myoclonus), and developmental delay. Children with type 5 Farber's disease survive into early childhood.
  Types 6 and 7 are very rare, and affected individuals have other associated disorders in addition to Farber's disease.

Farber lipogranulomatosis is a very rare disorder with only 80 cases having been reported worldwide. Most children with the classic form of Farber's disease die by age 2, usually from lung disease. Individuals having a milder form of the disease may live into their teenage years.

Currently there is no specific treatment for Farber's disease. Corticosteroids can help relieve pain. Nodes can be treated with bone marrow transplants, in certain instances, or may be surgically reduced or removed.

Mutations in the ASAH1 gene cause Farber's disease. The ASAH1 gene provides instructions for making an enzyme called acid ceramidase. Acid ceramidase breaks down fats called ceramides into a fat called sphingosine and a fatty acid. These two breakdown products are recycled to create new ceramides for the body to use. Mutations in the ASAH1 gene lead to severe reduction in acid ceramidase, typically to below 10 percent of normal. As a result, the enzyme cannot break down ceramides properly and they build up in the lysosomes of various cells, including in the lung, liver, colon, muscles used for movement such as skeletal muscles, cartilage, and bone. The buildup of ceramides along with the reduction of its fatty breakdown products in cells likely causes the signs and symptoms of Farber's disease.

Although there are attempts to apply diagnosis methods based on associated biochemical abnormalities there is an unmet need for a simple biochemical test exhibiting highly specific and highly sensitive detection of said lysosomal storage disease at an early stage and monitoring progression of the disease.

The identification of biomarkers for the early detection and diagnosis of Farber's disease is important for the correct diagnosis and prognosis of the disease. A biomarker should be technically feasible in many hands, easy to measure; useful, with a consistent, relative magnitude between affected and controls, reliable, and accurate clinically, and classifiable as strongly predictive or prognostic. Example of biomarkers specific for a certain LSD are, among others lyso-Gb1 for Gaucher's Disease, lyso-Gb3 for Fabry Disease and SM-509 for Nieamann Pick.

As to the biochemical diagnosis of Farber' disease it is to be noted that there is neither a biomarker specific for Farber's disease nor is there any biomarker currently in use for the detection of Faber's disease.

In light thereof, the problem underlying the present invention is the provision of a means for the diagnosis of Farber's disease. A further problem underlying the present invention is the provision of a means for the diagnosis of Farber's disease making use of a biomarker.

These and other problems are solved by the subject matter of the attached independent claims. Preferred embodiments may be taken from the attached dependent claims.

These and other problems are equally solved by the subject matter of the following embodiments 1 to 170 and further embodiments disclosed herein. It is to be taken into consideration that the subject matter of embodiments 1, 30, 54, 81, 101, 127, 158, 164, 168 and 170 is each also referred to as aspect of the present invention.

Embodiment 1

A method for diagnosing Farber's disease in a subject comprising
a step a), wherein the step a) comprises detecting a biomarker in a sample from the subject.

Embodiment 2

The method according to embodiment 1, wherein the method comprises a step b) wherein the step b) comprises determining a level of the biomarker present in the sample.

Embodiment 3

The method according to any one of embodiments 1 or 2, wherein the level of the biomarker is indicative whether or not the subject is suffering from Farber's disease or whether or not the subject is at risk of suffering from Farber's disease.

Embodiment 4

The method according to any one of embodiments 1 to 3, wherein the sample from the subject is a sample from a subject who has previously been treated for Farber's disease or a sample from a subject who has previously been diagnosed for Farber's disease.

Embodiment 5

The method according to any one of embodiments 1 to 3, wherein the sample from the subject is a sample from a subject who has not previously been treated for Farber's disease or a sample from a subject who has not been previously diagnosed for Farber's disease.

Embodiment 6

The method according to any one of embodiments 1 to 5, wherein the method comprises a step c), wherein the step c) comprises applying, maintaining, reducing, elevating or not applying a therapy based on whether the subject is suffering from Farber's disease or is at risk of suffering from Farber's disease.

Embodiment 7

The method according to embodiment 6, wherein the method comprises a step d), wherein the step d) comprises detecting the biomarker in a sample from the subject after a therapy has been applied, maintained, reduced, elevated or not applied in step c).

Embodiment 8

The method according to any one of embodiments 6 to 7, wherein the method comprises a step e), wherein the step e) comprises determining a level of the biomarker in the sample from the subject after a therapy has been applied, maintained, reduced, elevated or not applied in step c).

Embodiment 9

The method according to embodiment 8, wherein the method comprises a step f), wherein the step f) comprises determining whether the level of the biomarker determined in step b) is lower than the level of the biomarker determined in step e).

Embodiment 10

The method according to embodiment 9, wherein the method comprises a step g), wherein the step g) comprises applying, maintaining, reducing, elevating or not applying a therapy based on step 0.

Embodiment 11

The method according to any one of embodiments 1 to 10, wherein the biomarker is one selected from the group consisting of C26 ceramide, a medium ceramide and a long ceramide, wherein a medium ceramide is a ceramide of formula (2)

$$\text{(2)}$$

wherein n is any integer from: 8, 10, 12, 14 and 16 and
a long ceramide is a ceramide of formula (2)

$$\text{(2)}$$

wherein n is any integer from 18, 20 and 22.

Embodiment 12

The method according to embodiment 11, wherein the biomarker is C26 ceramide.

Embodiment 13

The method according to any one of embodiments 11 to 12, wherein the biomarker is cis-C26 ceramide of the following formula

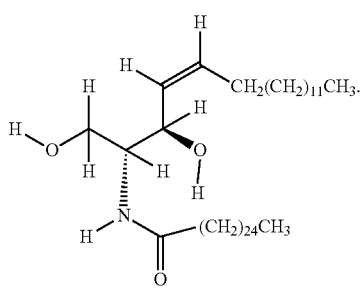

Embodiment 14

The method according to any one of embodiments 11 to 12, wherein the biomarker is total C26 ceramide, preferably total C26 ceramide is cis-C26 ceramide and trans-C26 ceramide.

Embodiment 15

The method according to any one of embodiments 11 to 14, wherein the method comprises determining the level of the biomarker in a or the sample, preferably the level of cis-C26 ceramide or the level of total C26 ceramide, wherein, preferably as used herein for each and any aspect of the invention, the level of total C26 ceramide is the sum of the level of cis-C26 ceramide and the level of trans-C26 ceramide.

Embodiment 16

The method according to any one of embodiments 1 to 15, wherein the biomarker is detected by means of immunoassay, mass spectrometric analysis, biochip array, functional nucleic acids and/or a fluorescent derivative of the biomarker.

Embodiment 17

The method according to embodiment 16, wherein the biomarker is detected by means of mass spectrometric analysis.

Embodiment 18

The method according to embodiment 17, wherein mass spectrometric analysis is selected from the group comprising SELDI MS, MALDI MS, ESI MS, DESI MS, ion mobility MS, electrospray ionization multiple reaction monitoring (ESI-MRM MS).

Embodiment 19

The method according to any one of embodiments 16 to 18, wherein mass spectrometric analysis uses an analyzer selected from the group comprising ToF, QToF, ion trap, Triple Quad, orbitrap, ion mobility and any combination thereof.

Embodiment 20

The method according to any one of embodiments 16 to 19, wherein the mass spectrometric analysis comprises or uses MS/MS, MRM, SRM or any combination thereof, preferably MS/MS, MS/MRM or MS/SRM.

Embodiment 21

The method according to any one of embodiments 1 to 20, wherein the method comprises protein precipitation from the sample and/or extraction of the biomarker from the sample.

Embodiment 22

The method according to any one of embodiments 1 to 21, wherein the method comprises protein precipitation from the sample.

Embodiment 23

The method according to any one of embodiments 21 to 22, wherein the method comprises HPLC.

Embodiment 24

The method according to embodiment 23, wherein the method comprises
a) protein precipitation from the sample and HPLC;
b) extraction of the biomarker from the sample and HPLC; and/or
c) protein precipitation from the sample, extraction of the biomarker from the sample and HPLC.

Embodiment 25

The method according to any one of embodiments 21 to 22, wherein the method further comprises at least one from the group consisting of HPLC, MS/MS, MRM and MS/MS-MRM.

Embodiment 26

The method according to embodiment 25, wherein the method comprises
a) protein precipitation from the sample, HPLC and MS/MS or MRM;
b) protein precipitation from the sample, HPLC and MS/MS-MRM;
c) extraction of the biomarker from the sample, HPLC and MS/MS or MRM;
d) extraction of the biomarker from the sample, HPLC and MS/MS-MRM;
e) protein precipitation and extraction of the biomarker from the sample, HPLC and MS/MS or MRM; and/or
f) protein precipitation and extraction of the biomarker from the sample, HPLC and MS/MS-MRM.

Embodiment 27

The method according to any one of embodiments 1 to 26, wherein the subject is a human.

Embodiment 28

The method according to embodiment 27, wherein the subject is a subject suffering from any one of type 1 of Farber's disease, type 2 of Farber's disease, type 3 of Farber's disease, type 4 of Farber's disease, type 5 of Farber's disease, type 6 of Farber's disease or type 7 of Farber's disease.

Embodiment 29

The method according to any one of embodiments 7 to 28, wherein step d) comprising detecting the biomarker in a sample comprises subjecting the sample to a protein precipitation and/or biomarker extraction step, precipitating protein and/or extraction biomarker from the sample, providing a supernatant of the sample, subjecting the supernatant of the sample to HPLC and MS/MS and determining the level of the biomarker present in the supernatant of the sample.

Embodiment 30

A method for diagnosing Farber's disease in a subject, wherein the method comprises the following steps:
i) adding an internal standard to a sample from the subject, wherein the sample from the subject is selected from the group comprising plasma, serum and blood;
ii) optionally mixing the sample containing the internal standard;
iii) subjecting the sample to a protein precipitation and/or a biomarker extraction step, whereby protein from the sample is precipitated and/or the biomarker is extracted and a first supernatant of the sample is provided;
iv) optionally subjecting the first supernatant of the sample or at least a part thereof to a first separation step which provides a second supernatant, whereby preferably the first separation step is a step of centrifugation;
v) subjecting the first supernatant and/or the second supernatant, or at least a part thereof, to a second separation step, wherein the second separation step comprises injecting at least a part of the first supernatant and/or at least a part of the second supernatant into an HPLC-MS/MS system and using an HPLC column with a gradient from acidic water to acetonitrile/acetone; wherein the HPLC column is preferably an HPLC column selected from the group comprising a C8 HPLC column and a C18 HPLC column, and wherein the second separation step provides a separated sample;
vi) subjecting the separated sample to MS/MS, wherein MS/MS comprises electrospray ionization and Multiple Reacting Monitoring;
and wherein the method comprises
a step a), wherein the step a) comprises detecting a biomarker in a sample from the subject, and optionally
a step b), wherein the step b) comprises determining a level of the biomarker present in the sample, and
wherein the method is otherwise preferably a method according to any one of embodiments 1 to 29.

Embodiment 31

The method according to embodiment 30, wherein the internal standard is selected from the group comprising N-lauroyl sphingosine, lyso-Gb2, a C17 ceramide, a C19 ceramide, a C21 ceramide, a C23 ceramide and a C25 ceramide.

Embodiment 32

The method according to any one of embodiments 1 to 31, wherein step b), step c) and/or step e) comprises comparing the level of the biomarker in the sample with a cut-off value.

Embodiment 33

The method according to embodiment 32, wherein if the level of the biomarker in the sample from the subject is higher than the cut-off value this is indicative that the subject is suffering from Farber's disease or is at risk of suffering from Farber's disease.

Embodiment 34

The method according to embodiment 32, wherein if the level of the biomarker in the sample from the subject is lower than the cut-off value this is indicative that the subject is not suffering from or is not at risk of suffering from Farber's disease.

Embodiment 35

The method according to any one of embodiments 32 to 34, wherein the cut-off value is selected such that a or the sensitivity for diagnosing Farber's disease in a subject is from about 95% to 100%, preferably from about 98.5% to 100% more preferably 99.5% to 100%.

Embodiment 36

The method according to any one of embodiments 1 to 35, wherein step b) and/or step c) and/or step e) comprises that a level of the biomarker in said subject is compared to a level of the biomarker detected in a sample from a control sample;

Embodiment 37

The method according to embodiment 36, wherein the control sample is a sample from a subject not having Farber's disease.

Embodiment 38

The method according to any one of embodiments 36 to 37, wherein if the level of the biomarker in the sample from the subject is higher than the level of the biomarker in the control sample this is indicative that the subject is suffering from and/or is at risk of suffering from Farber's disease.

Embodiment 39

The method according to any one of embodiments 1 to 38, wherein the sample from the subject is selected from the group comprising blood, a blood product, urine, saliva, cerebrospinal fluid, stool, tissue sample and lymph.

Embodiment 40

The method according to embodiment 39, wherein the sample from the sample from the subject is selected from the group comprising blood and a blood product.

Embodiment 41

The method according to any one of embodiments 39 to 40, wherein the blood product is dried blood spots (DBS).

Embodiment 42

The method according to any one of embodiments 1 to 41, preferably 41, wherein the method has a limit of detection for C26 ceramide of 0.1 ng/mL, wherein, preferably, the biomarker is detected by means of mass spectrometry.

Embodiment 43

The method according to any one of embodiments 32 to 42, wherein the method is for the diagnosis of Farber's disease and wherein the cut-off value is about 69 nmol/L, preferably 69.0 nmol/l, in case the biomarker is total C26 ceramide and the cut-off value is about 28 nmol/L, preferably 28.3 nmol/L, in case the biomarker is cis-C26 ceramide.

Embodiment 44

The method of any one of embodiments 32 and 43, wherein the cut-off value is a reference cut-off value.

Embodiment 45

The method of any one of embodiments 32 to 44, wherein the cut-off value is a cut-off value adjusted to the reference cut-off value.

Embodiment 46

The method of any one of embodiments 43 to 45, wherein the sample from the subject is dried blood spots (DBS).

Embodiment 47

The method according to any one of embodiments 1 to 46, wherein the subject has been previously treated for Farber's disease and/or wherein the subject has been previously diagnosed for Farber's disease.

Embodiment 48

The method according to any one of embodiments 1 to 47, wherein the subject has not been previously treated for Farber's disease and/or wherein the subject has not been previously diagnosed for Farber's disease.

Embodiment 49

The method according to any one of embodiments 30 to 48, wherein the method comprises
a step c), wherein the step c) comprises applying, maintaining, reducing, elevating or not applying a therapy based on whether the subject is suffering from Farber's disease or is at risk of suffering from Farber's disease.

Embodiment 50

The method according to any one of embodiments 30 to 48, wherein the method comprises a step d), wherein the step d) comprises detecting the biomarker in a sample from the subject after a therapy has been applied, maintained, reduced, elevated or not applied in step c).

Embodiment 51

The method according to any one of embodiments 30 to 50, wherein the method comprises a step e), wherein the step e) comprises determining a level of the biomarker in the sample from the subject after a therapy has been applied, maintained, reduced, elevated or not applied in step c).

Embodiment 52

The method according to any one of embodiments 30 to 51, wherein the method comprises a step f), wherein the step f) comprises determining whether the level of the biomarker determined in step b) is lower than the level of the biomarker determined in step f).

Embodiment 53

The method according to any embodiment 52, wherein the method comprises
a step g), wherein the step g) comprises applying, maintaining, reducing, elevating or not applying a therapy based on step f).

Embodiment 54

A method for determining the effectiveness of at least one treatment applied to a subject being positively tested for suffering from or being at risk of suffering from Farber's disease comprising
a step a), wherein the step a) comprises determining at several points in time a level of a biomarker in a sample from the subject, wherein the biomarker is preferably one selected from the group consisting of C26 ceramide, a medium ceramide and a long ceramide, wherein a medium ceramide is a ceramide of formula (2)

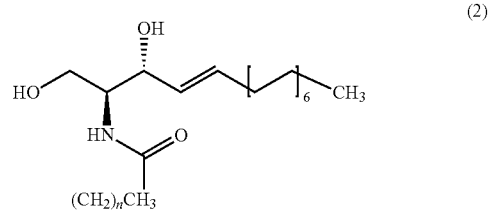

wherein n is any integer from: 8, 10, 12, 14 and 16 and a long ceramide is a ceramide of formula (2)

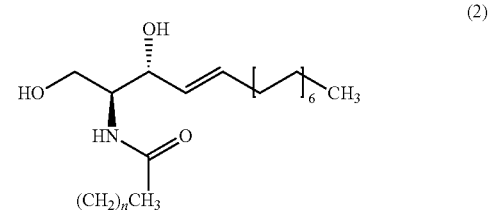

wherein n is any integer from 18, 20 and 22.

Embodiment 55

The method according to embodiment 54, wherein the biomarker is C26 ceramide.

Embodiment 56

The method according to any one of embodiments 54 to 55, wherein the biomarker is cis-C26 ceramide of the following formula

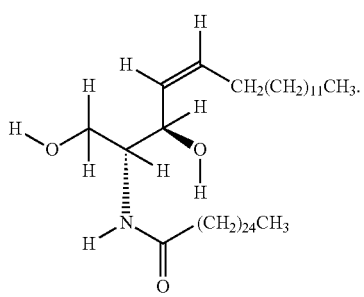

Embodiment 57

The method according to any one of embodiments 54 to 55, wherein the biomarker is total C26 ceramide, preferably total C26 ceramide is cis-C26 ceramide and trans-C26 ceramide.

Embodiment 58

The method according to any one of embodiments 54 to 57, wherein the method comprises determining the level of the biomarker in a or the sample, preferably the level of cis-C26 ceramide or the level of total C26 ceramide, wherein, preferably as used herein for each and any aspect of the invention, the level of total C26 ceramide is the sum of the level of cis-C26 ceramide and the level of trans-C26 ceramide.

Embodiment 59

The method according to any one of embodiments 54 to 58, wherein the subject has been previously treated for Farber's disease or diagnosed for Farber's disease.

Embodiment 60

The method according to any one of embodiments 54 to 58, wherein the subject has not been previously treated for Farber's disease or wherein the subject has not been previously diagnosed for Farber's disease.

Embodiment 61

The method according to any one of embodiments 54 to 60, wherein the method comprises a step b), wherein the step b) comprises applying, maintaining, reducing, elevating or not applying at least one treatment applied to the subject based on the decrease in the level of the biomarker as determined in step a)

Embodiment 62

The method according to any one of embodiments 54 to 61, wherein the method comprises a step c), wherein the step c) comprises detecting the biomarker in the sample from the subject, wherein the sample has been taken prior to the beginning of the treatment after applying, maintaining, reducing, elevating or not applying at least one treatment in step b) and, optionally determining a level of a biomarker present in a sample from the subject,

Embodiment 63

The method according to any one of embodiments 1 to 62, wherein the treatment and/or therapy is selected from the group comprising enzyme replacement therapy, substrate reduction therapy, chaperone therapy, gene therapy, stem cell transplantation and DNA/RNA skipping.

Embodiment 64

The method according to any one of embodiments 54 to 62, wherein the method comprises a step d), wherein the step d) comprises determining whether the level of the biomarker determined in step a) is lower than the level of the biomarker determined in step c);

Embodiment 65

The method according to embodiment 64, wherein the method comprises
a step e), wherein step e) comprises applying, maintaining, reducing, elevating or not applying at least one treatment applied to the subject based on step d).

Embodiment 66

The method according to any one of embodiments 54 to 65, wherein the biomarker is detected by means of immunoassay, mass spectrometric analysis, biochip array, functional nucleic acids and/or a fluorescent derivative of the biomarker.

Embodiment 67

The method according to embodiment 66, wherein the biomarker is detected by means of mass spectrometric analysis.

Embodiment 68

The method according to embodiment 67, wherein the biomarker is detected by means of mass spectrometric analysis.

Embodiment 69

The method according to embodiment 67, wherein mass spectrometric analysis is selected from the group comprising SELDI MS, MALDI MS, ESI MS, DESI MS, ion mobility MS, electrospray ionization multiple reaction monitoring (ESI-MRM MS).

Embodiment 70

The method according to any one of embodiments 67 to 69, wherein mass spectrometric analysis uses an analyzer selected from the group comprising ToF, QToF, ion trap, Triple Quad, orbitrap, ion mobility and any combination thereof.

Embodiment 71

The method according to any one of embodiments 67 to 70, wherein the mass spectrometric analysis comprises or uses MS/MS, MRM, SRM or any combination thereof, preferably MS/MS, MS/MRM or MS/SRM.

Embodiment 72

The method according to any one of embodiments 54 to 71, wherein the method comprises protein precipitation from the sample and/or extraction of the biomarker from the sample.

Embodiment 73

The method according to any one of embodiments 54 to 72, wherein the method comprises protein precipitation from the sample.

Embodiment 74

The method according to any one of embodiments 72 to 73, wherein the method comprises HPLC.

Embodiment 75

The method according to embodiment 74, wherein the method comprises
a) protein precipitation from the sample and HPLC;
b) extraction of the biomarker from the sample and HPLC; and/or
c) protein precipitation from the sample, extraction of the biomarker from the sample and HPLC.

Embodiment 76

The method according to any one of embodiments 72 to 73, wherein the method further comprises at least one from the group consisting of HPLC, MS/MS, MRM and MS/MS-MRM.

Embodiment 77

The method according to embodiment 76, wherein the method comprises
a) protein precipitation from the sample, HPLC and MS/MS or MRM;
b) protein precipitation from the sample, HPLC and MS/MS.MRM;
c) extraction of the biomarker from the sample, HPLC and MS/MS or MRM;
d) extraction of the biomarker from the sample, HPLC and MS/MS-MRM;
e) protein precipitation and extraction of the biomarker from the sample, HPLC and MS/MS or MRM; and/or
f) protein precipitation and extraction of the biomarker from the sample, HPLC and MS/MS.MRM.

Embodiment 78

The method according to any one of embodiments 54 to 77, wherein the subject is a human.

Embodiment 79

The method according to embodiment 78, wherein the subject is a subject suffering from any one of type 1 of Farber's disease, type 2 of Farber's disease, type 3 of Farber's disease, type 4 of Farber's disease, type 5 of Farber's disease, type 6 of Farber's disease or type 7 of Farber's disease.

Embodiment 80

The method according to any one of embodiments 54 to 79, wherein the step of detecting the biomarker in the sample from the subject comprises precipitating protein and/or biomarker extraction from the sample from the subject, wherein precipitating protein and/or extracting biomarker from the sample provides a supernatant of the sample; subjecting a volume of the supernatant to HPLC and MS/MS and determining the level of the biomarker that is present in the sample from the subject.

Embodiment 81

A method of determining the effectiveness of a compound for the treatment of Farber's disease, wherein the method comprises the following steps:
a) determining a level of a biomarker in a sample from a subject having Farber's disease;
b) administering to said subject said compound;
c) determining the level of the biomarker in a sample from the subject after the compound has been administered to the subject; and
d) determining whether the level of the biomarker determined in step c) is lower than the level of the biomarker determined in step a);
wherein if a level of the biomarker determined in step c) is lower than the level of the biomarker determined in step a) this indicates the effectiveness of said compound.

Embodiment 82

The method of embodiment 81, wherein the biomarker is one selected from the group consisting of C26 ceramide, a medium ceremide and a long ceramide, wherein a medium ceramide is a ceramide of formula (2)

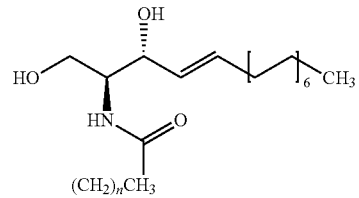

(2)

wherein n is any integer from: 8, 10, 12, 14 and 16 and a long ceramide is a ceramide of formula (2)

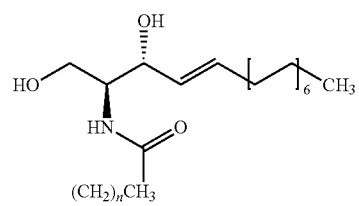

(2)

wherein n is any integer from 18, 20 and 22.

Embodiment 83

The method according to embodiment 82, wherein the biomarker is C26 ceramide.

Embodiment 84

The method according to any one of embodiments 82 to 83, wherein the biomarker is cis-C26 ceramide of the following formula

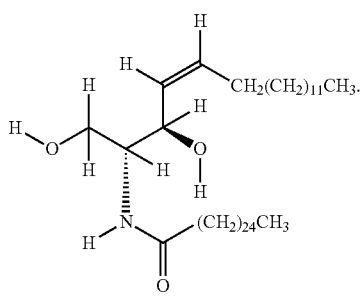

Embodiment 85

The method according to any one of embodiments 82 to 83, wherein the biomarker is total C26 ceramide, preferably total C26 ceramide is cis-C26 ceramide and trans-C26 ceramide.

Embodiment 86

The method according to any one of embodiments 82 to 85, wherein the method comprises determining the level of the biomarker in a or the sample, preferably the level of cis-C26 ceramide or the level of total C26 ceramide, wherein, preferably as used herein for each and any aspect of the invention, the level of total C26 ceramide is the sum of the level of cis-C26 ceramide and the level of trans-C26 ceramide.

Embodiment 87

The method according to any of embodiments 81 to 86, wherein the method comprises determining a level of the biomarker in a control sample.

Embodiment 88

The method according to any one of embodiments 81 to 87, wherein the biomarker is detected by means of immunoassay, mass spectrometric analysis, biochip array, functional nucleic acids and/or a fluorescent derivative of the biomarker.

Embodiment 89

The method according to embodiment 88, wherein the biomarker is detected by means of mass spectrometric analysis.

Embodiment 90

The method according to embodiment 89, wherein mass spectrometric analysis is selected from the group comprising SELDI MS, MALDI MS, ESI MS, DESI MS, ion mobility MS, and electrospray ionization multiple reaction monitoring (ESI-MRM MS).

Embodiment 91

The method according to any one of embodiments 88 to 90, wherein mass spectrometric analysis uses an analyzer selected from the group comprising ToF, QToF, ion trap, Triple Quad, orbitrap, ion mobility and any combination thereof.

Embodiment 92

The method according to any one of embodiments 88 to 91, wherein the mass spectrometric analysis comprises or uses MS/MS, MRM, SRM or any combination thereof, preferably MS/MS, MS/MRM or MS/SRM.

Embodiment 93

The method according to any one of embodiments 81 to 92, wherein the method comprises protein precipitation from the sample and/or extraction of the biomarker from the sample.

Embodiment 94

The method according to any one of embodiments 81 to 93, wherein the method comprises protein precipitation from the sample.

Embodiment 95

The method according to any one of embodiments 92 to 94, wherein the method comprises HPLC.

Embodiment 96

The method according to embodiment 95, wherein the method comprises
a) protein precipitation from the sample and HPLC;
b) extraction of the biomarker from the sample and HPLC; and/or
c) protein precipitation from the sample, extraction of the biomarker from the sample and HPLC.

Embodiment 97

The method according to any one of embodiments 93 to 94, wherein the method further comprises at least one from the group consisting of HPLC, MS/MS, MRM and MS/MS-MRM.

Embodiment 98

The method according to embodiment 97, wherein the method comprises
a) protein precipitation from the sample, HPLC and MS/MS or MRM;
b) protein precipitation from the sample, HPLC and MS/MS.MRM;
c) extraction of the biomarker from the sample, HPLC and MS/MS or MRM;
d) extraction of the biomarker from the sample, HPLC and MS/MS.MRM;
e) protein precipitation and extraction of the biomarker from the sample, HPLC and MS/MS or MRM; and/or
f) protein precipitation and extraction of the biomarker from the sample, HPLC and MS/MS.MRM.

Embodiment 99

The method according to any one of embodiments 81 to 98, wherein the subject is a human.

Embodiment 100

The method according to embodiment 99, wherein the subject is a subject suffering from any one of type 1 of Farber's disease, type 2 of Farber's disease, type 3 of Farber's disease, type 4 of Farber's disease, type 5 of Farber's disease, type 6 of Farber's disease or type 7 of Farber's disease.

Embodiment 101

A method for determining the course of Farber's disease in a subject comprising the step of
a) determining at several points in time a level of a biomarker present in a sample from the subject.

Embodiment 102

The method according to embodiment 101, wherein the subject has been previously treated or diagnosed for Farber's disease.

Embodiment 103

The method according to embodiment 101, wherein the subject has not been previously treated or wherein the subject has not been previously diagnosed for Farber's disease.

Embodiment 104

The method according to any one of embodiments 101 to 103, further comprising a step of
b) applying, maintaining, reducing, elevating or not applying a therapy based on the diagnosis of whether the subject is suffering from or for being at risk for developing Farber's.

Embodiment 105

The method according to any one of embodiments 101 to 104, further comprising a step of
c) detecting the biomarker in a sample from the subject after applying, maintaining, reducing, elevating or not applying a therapy in a step of b).

Embodiment 106

The method according to any one of embodiments 101 to 105, further comprising a step of
d) determining a level of the biomarker in the sample from the subject after applying, maintaining, reducing, elevating or not applying a therapy in a step of b).

Embodiment 107

The method according to any one of embodiments 101 to 106, further comprising the steps of
e) determining whether the level of the biomarker determined in step a) is lower than the level of the biomarker determined in step d);

Embodiment 108

The method according to any embodiment 107, further comprising the step of
f) applying, maintaining, reducing, elevating or not applying a therapy based on the step of e).

Embodiment 109

The method according to any one of embodiments 101 to 108, wherein the biomarker is one selected from the group consisting of C26 ceramide, a medium ceramide and a long ceramide, wherein a medium ceramide is a ceramide of formula (2)

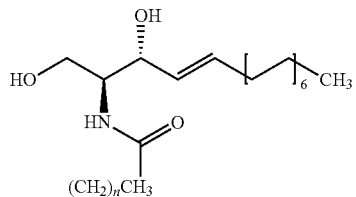

wherein n is any integer from: 8, 10, 12, 14 and 16 and a long ceramide is a ceramide of formula (2)

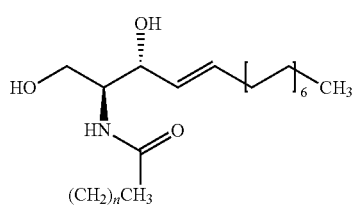

wherein n is any integer from 18, 20 and 22.

Embodiment 110

The method according to embodiment 109, wherein the biomarker is C26 ceramide.

Embodiment 111

The method according to any one of embodiments 109 to 110, wherein the biomarker is cis-C26 ceramide of the following formula

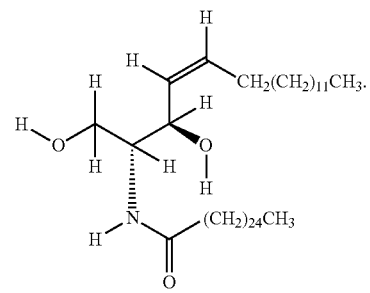

Embodiment 112

The method according to any one of embodiments 109 to 110, wherein the biomarker is total C26 ceramide, preferably total C26 ceramide is cis-C26 ceramide and trans-C26 ceramide.

Embodiment 113

The method according to any one of embodiments 109 to 112, wherein the method comprises determining the level of the biomarker in a or the sample, preferably the level of cis-C26 ceramide or the level of total C26 ceramide, wherein, preferably as used herein for each and any aspect of the invention, the level of total C26 ceramide is the sum of the level of cis-C26 ceramide and the level of trans-C26 ceramide.

Embodiment 114

The method according to any one of embodiments 101 to 113, wherein the biomarker is detected by means of immunoassay, mass spectrometric analysis, biochip array, functional nucleic acids and/or a fluorescent derivative of the biomarker.

Embodiment 115

The method according to embodiment 114, wherein the biomarker is detected by means of mass spectrometric analysis.

Embodiment 116

The method according to embodiment 115, wherein mass spectrometric analysis is selected from the group comprising SELDI MS, MALDI MS, ESI MS, DESI MS, ion mobility MS and electrospray ionization multiple reaction monitoring (ESI-MRM MS).

Embodiment 117

The method according to any one of embodiments 114 to 116, where in mass spectrometric analysis uses an analyzer selected from the group comprising ToF, QToF, ion trap, Triple Quad, orbitrap, ion mobility and any combination thereof.

Embodiment 118

The method according to any one of embodiments 114 to 117, wherein the mass spectrometric analysis comprises, or uses MS/MS, MRM, SRM or any combination thereof, preferably MS/MS, MS/MRM or MS/SRM.

Embodiment 119

The method according to any one of embodiments 101 to 118, wherein the method comprises protein precipitation from the sample and/or extraction of the biomarker from the sample.

Embodiment 120

The method according to any one of embodiments 101 to 119, wherein the method comprises protein precipitation from the sample.

Embodiment 121

The method according to any one of embodiments 119 to 120, wherein the method comprises HPLC.

Embodiment 122

The method according to embodiment 121, wherein the method comprises
a) protein precipitation from the sample and HPLC;
b) extraction of the biomarker from the sample and HPLC; and/or
c) protein precipitation from the sample, extraction of the biomarker from the sample and HPLC.

Embodiment 123

The method according to any one of embodiments 119 to 120, wherein the method further comprises at least one from the group consisting of HPLC, MS/MS, MRM and MS/MS-MRM.

Embodiment 124

The method according to embodiment 123, wherein the method comprises
a) protein precipitation from the sample, HPLC and MS/MS or MRM;
b) protein precipitation from the sample, HPLC and MS/MS.MRM;
c) extraction of the biomarker from the sample, HPLC and MS/MS or MRM;
d) extraction of the biomarker from the sample, HPLC and MS/MS-MRM;
e) protein precipitation and extraction of the biomarker from the sample, HPLC and MS/MS or MRM; and/or
f) protein precipitation and extraction of the biomarker from the sample, HPLC and MS/MS-MRM.

Embodiment 125

The method according to any one of embodiments 101 to 124, wherein the subject is a human.

Embodiment 126

The method according to embodiment 125, wherein the subject is a subject suffering from any one of type 1 of Farber's disease, type 2 of Farber's disease, type 3 of Farber's disease, type 4 of Farber's disease, type 5 of Farber's disease, type 6 of Farber's disease or type 7 of Farber's disease.

Embodiment 127

A method for the treatment of a subject suffering from or being at risk of developing Farber's disease, wherein the method comprises
a) performing an assay to detect a biomarker in a sample from the subject;
b) determining the level of the biomarker present in the sample;
c) comparing the level of the biomarker present in the sample to a cut-off value; and
d) treating the subject with a therapy if the level of the biomarker present in the sample is higher than the cut-off value.

Embodiment 128

The method of embodiment 127, wherein the therapy is selected from the group comprising administration of a corticosteroid to the subject, enzyme replacement therapy, gene therapy, bone marrow transplantation, substrate reduction therapy, chaperone therapy, stem cell transplantation and DNA/RNA skipping Embodiment 129

The method of embodiment 128, wherein the enzyme is acid ceramidase.

Embodiment 130

The method of embodiment 128, wherein gene therapy comprises introducing a nucleic acid coding for and/or providing expression of ASAH1 or a derivative thereof.

Embodiment 131

The method of embodiment 129, wherein the nucleic acid is introduced into the subject for permanent expression of acid ceramidase.

Embodiment 132

The method of embodiment 129, wherein the nucleic acid is introduced into the subject for transient expression of acid ceramidase.

Embodiment 133

The method of any one of embodiments 129 to 132, wherein the nucleic acid is an expression vector or an mRNA.

Embodiment 134

The method of any one of embodiments 127 to 133, wherein the assay to detect a biomarker is or makes use of a method for diagnosing Farber's disease, preferably a method according to any one of embodiments 1 to 53.

Embodiment 135

The method according to any one of embodiments 127 to 134, wherein the biomarker is one selected from the group consisting of C26 ceramide, a medium ceramide and a long ceramide, wherein a medium ceramide is a ceramide of formula (2)

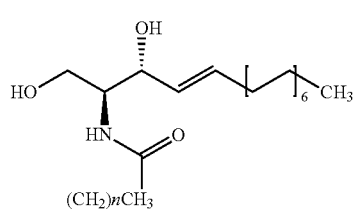

(2)

wherein n is any integer from: 8, 10, 12, 14 and 16 and a long ceramide is a ceramide of formula (2)

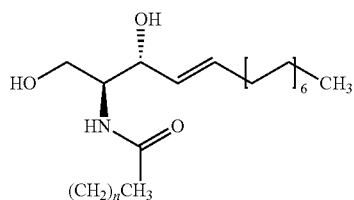

(2)

wherein n is any integer from 18, 20 and 22.

Embodiment 136

The method according to embodiment 135, wherein the biomarker is C26 ceramide.

Embodiment 137

The method according to any one of embodiments 135 to 136, wherein the biomarker is cis-C26 ceramide of the following formula

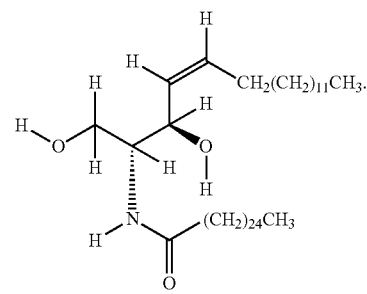

Embodiment 138

The method according to any one of embodiments 135 to 136, wherein the biomarker is total C26 ceramide, preferably total C26 ceramide is cis-C26 ceramide and trans-C26 ceramide.

Embodiment 139

The method according to any one of embodiments 135 to 138, wherein the method comprises determining the level of the biomarker in a or the sample, preferably the level of cis-C26 ceramide or the level of total C26 ceramide, wherein, preferably as used herein for each and any aspect of the invention, the level of total C26 ceramide is the sum of the level of cis-C26 ceramide and the level of trans-C26 ceramide.

Embodiment 140

The method according to any one of embodiments 127 to 139, wherein assay is selected from the group comprising an immunoassay, mass spectrometric analysis, a biochip array, a functional nucleic acid, antibody and/or a fluorescent derivative of the biomarker; preferably the functional nucleic acid is an aptamer or a spiegelmer.

Embodiment 141

The method according to embodiment 140, wherein the biomarker is detected by means of mass spectrometric analysis.

Embodiment 142

The method according to embodiment 141, wherein mass spectrometric analysis is selected from the group comprising SELDI MS, MALDI MS, ESI MS, DESI MS, ion mobility MS, electrospray ionization multiple reaction monitoring (ESI-MRM MS).

Embodiment 143

The method according to any one of embodiments 140 to 142, wherein mass spectrometric analysis uses an analyzer selected from the group comprising ToF, QToF, ion trap, Triple Quad, orbitrap, ion mobility and any combination thereof.

Embodiment 144

The method according to any one of embodiments 140 to 143, wherein the mass spectrometric analysis comprises or uses MS/MS, MRM, SRM or any combination thereof, preferably MS/MS, MS/MRM or MS/SRM.

Embodiment 145

The method according to any one of embodiments 127 to 144, wherein the method comprises protein precipitation from the sample and/or extraction of the biomarker from the sample.

Embodiment 146

The method according to any one of embodiments 127 to 145, wherein the method comprises protein precipitation from the sample.

Embodiment 147

The method according to any one of embodiments 145 to 146, wherein the method comprises HPLC.

Embodiment 148

The method according to embodiment 147, wherein the method comprises
a) protein precipitation from the sample and HPLC;
b) extraction of the biomarker from the sample and HPLC; and/or
c) protein precipitation from the sample, extraction of the biomarker from the sample and HPLC.

Embodiment 149

The method according to any one of embodiments 145 to 146, wherein the method further comprises at least one from the group consisting of HPLC, MS/MS, MRM and MS/MS-MRM.

Embodiment 150

The method according to embodiment 149, wherein the method comprises
a) protein precipitation from the sample, HPLC and MS/MS or MRM;
b) protein precipitation from the sample, HPLC and MS/MS-MRM;
c) extraction of the biomarker from the sample, HPLC and MS/MS or MRM;
d) extraction of the biomarker from the sample, HPLC and MS/MS-MRM;
e) protein precipitation and extraction of the biomarker from the sample, HPLC and MS/MS or MRM; and/or
f) protein precipitation and extraction of the biomarker from the sample, HPLC and MS/MS-MRM.

Embodiment 151

The method according to any one of embodiments 127 to 150, wherein the subject is a human.

Embodiment 152

The method according to embodiment 151, wherein the subject is a subject suffering from any one of type 1 of Farber's disease, type 2 of Farber's disease, type 3 of Farber's disease, type 4 of Farber's disease, type 5 of Farber's disease, type 6 of Farber's disease or type 7 of Farber's disease.

Embodiment 153

The method according to any one of embodiments 127 to 152, wherein step d) comprising detecting the biomarker in a sample comprises subjecting the sample to a protein precipitation and/or biomarker extraction step, precipitating protein and/or extraction biomarker from the sample, providing a supernatant of the sample, subjecting the supernatant of the sample to HPLC and MS/MS and determining the level of the biomarker present in the supernatant of the sample.

Embodiment 154

The method according to any one of embodiments 127 to 153, wherein the cut-off value is about 69 nmol/L, preferably 69.0 nmol/1, in case the biomarker is total C26 ceramide and the cut-off value is about 28 nmol/L, preferably 28.3 nmol/L, in case the biomarker is cis-C26 ceramide.

Embodiment 155

The method of any one of embodiments 127 to 154, wherein the cut-off value is a reference cut-off value.

Embodiment 156

The method of any one of embodiments 127 to 155, wherein the cut-off value is a cut-off value adjusted to the reference cut-off value.

Embodiment 157

The method of any one of embodiments 127 to 156, wherein the sample from the subject is dried blood spots (DBS).

Embodiment 158

Use of mass spectrometric analysis for the detection of a biomarker, wherein the biomarker is selected from the group consisting of C26 ceramide, a medium ceramide and a long ceramide, wherein a medium ceramide is a ceramide of formula (2)

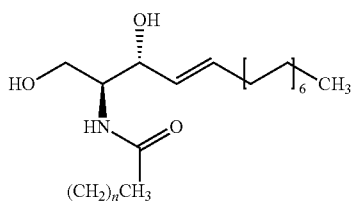

(2)

wherein n is any integer from: 8, 10, 12, 14 and 16 and a long ceramide is a ceramide of formula (2)

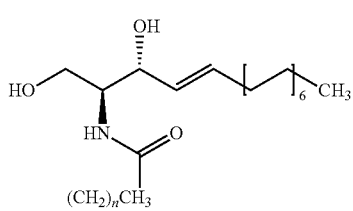

(2)

wherein n is any integer from 18, 20 and 22.

Embodiment 159

Use according to embodiment 158, wherein the biomarker is C26 ceramide.

Embodiment 160

Use according to any one of embodiments 158 to 129, wherein the biomarker is cis-C26 ceramide of the following formula

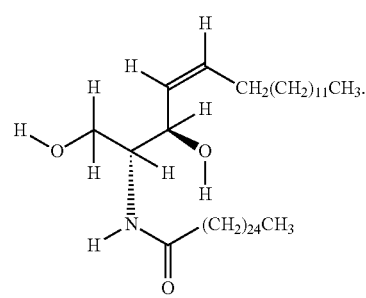

Embodiment 161

Use according to any one of embodiments 158 to 159, wherein the biomarker is total C26 ceramide, preferably total C26 ceramide is cis-C26 ceramide and trans-C26 ceramide.

Embodiment 162

Use according to any one of embodiments 158 to 161, wherein the detection comprises the use of HPLC.

Embodiment 163

Use according to any one of embodiments 158 to 162, wherein the mass spectrometric analysis comprises or uses MS/MS.

Embodiment 164

Use of a biomarker for the diagnosis of Farber's disease, preferably in a method according to any one of the preceding embodiments, wherein the biomarker is selected from the group consisting of C26 ceramide, a medium ceramide and a long ceramide, wherein a medium ceramide is a ceramide of formula (2)

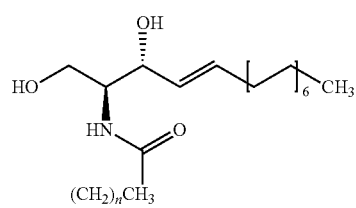

(2)

wherein n is any integer from: 8, 10, 12, 14 and 16 and a long ceramide is a ceramide of formula (2)

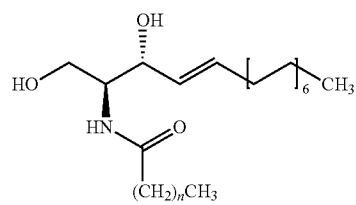

(2)

wherein n is any integer from 18, 20 and 22.

Embodiment 165

Use according to embodiment 164, wherein the biomarker is C26 ceramide.

Embodiment 166

Use according to any one of embodiments 164 to 165, wherein the biomarker is cis-C26 ceramide of the following formula

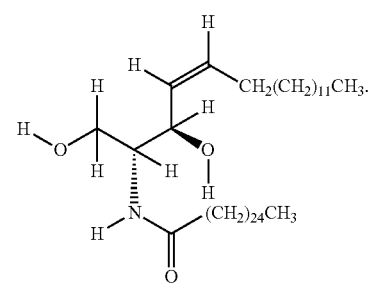

Embodiment 167

Use according to any one of embodiments 164 to 165, wherein the biomarker is total C26 ceramide, preferably total C26 ceramide is cis-C26 ceramide and trans-C26 ceramide.

Embodiment 168

A kit for determining the presence of a biomarker in a sample from a subject, wherein the kit comprises
a) an interaction partner of the biomarker;
b) optionally a solid support comprising at least one capture reagent attached thereto, wherein the capture reagent binds the biomarker; and
c) instructions for using the solid support to detect the biomarker,
wherein the biomarker is C26 ceramide, preferably cis-C26 ceramide.

Embodiment 169

The kit according to embodiment 168, wherein the kit is for
a) use in a method for diagnosing Farber's disease;
b) use in a method for determining the course of Farber's disease in a subject;
c) use in a method for determining the effectiveness of at least one treatment applied to a subject, and/or
d) a method for the treatment of a subject suffering from or being at risk of developing Farber's disease,
wherein preferably the method of a), b), c) and/or d) is a method according to any one of the preceding embodiments.

Embodiment 170

Use of a compound selected from the group consisting of N-lauroyl sphingosine, lyso-Gb2, a C17 ceramide, a C19 ceramide, a C21 ceramide, a C23 ceramide and a C25 ceramide as an internal standard in
a) use in a method for diagnosing Farber's disease;
b) use in a method for determining the course of Farber's disease in a subject;
c) use in a method for determining the effectiveness of at least one treatment applied to a subject; and/or
d) a method for the treatment of a subject suffering from or being at risk of developing Farber's disease,
wherein preferably the method of a), b), c) and/or d) is a method according to any one of the preceding embodiments.

The present inventors have surprisingly found that compound C26 ceramide constitutes a biomarker which allows for a method for diagnosing Farber's disease in a subject, more specifically diagnosing Farber's disease in a subject with high specificity and sensitivity using said C26 ceramide as the biomarker. In a preferred embodiment of the present invention C26 ceramide is cis-C26 ceramide. In a further embodiment of the present invention C26 ceramide is total C26 ceramide. In light of these embodiments, it is within the present invention that whenever it is referred to C26 ceramide, such reference also includes any embodiment of C26 ceramide, including cis-C26 ceramide and total C26 ceramide.

The present inventors have also surprisingly found that the level of C26 ceramide and cis-C26 ceramide in particular, determined in the sample from a subject by the methods of the present invention allows for diagnosing Farber's disease with high sensitivity and high specificity.

Furthermore, the present inventors have also surprisingly found that C26 ceramide and cis-C26 ceramide in particular, which can be detected by the methods of the present invention, is circulating in the blood of a subject. Moreover, the present inventors have surprisingly found that C26 ceramide and cis-C26 ceramide in particular, which is present in the blood of a subject is useful in a method for diagnosing Farber's disease in a subject comprising a step of detecting a biomarker in a sample from the subject, wherein the biomarker is C26 ceramide and cis-C26 ceramide in particular. The present inventors have also surprisingly found that the level of C26 ceramide and cis-C26 ceramide in particular determined in the sample from a subject by the methods of the present invention allows for diagnosing Farber's disease with high sensitivity and high specificity.

In connection with the instant invention it is referred to the concentration or level of C26 ceramide. Such concentration or level of C26 ceramide is preferably determined as follows. In the analytical set-up as described in the example part in more detail an internal standard is added to the sample to be analyzed. In the course of such analysis a chromatogram is obtained indicating as individual peaks the various compounds detected in the sample. The various compounds include, among others, C26 ceramide and the internal standard. In order to determine from such chromatogram and the peaks indicated therein the concentration or level of C26 ceramide the peak area of the peak corresponding to C26 ceramide and the peak area of the peak corresponding to the internal standard is determined. The concentration of C26 ceramide is obtained using a standard curve of the C26 ceramide at different concentrations in the presence of internal standard at known concentration. In those embodiments of the methods of the present invention where the concentration or level of C26 ceramide is used, the concentration of C26 ceramide is preferably the normalized concentration of C26 ceramide.

The term "lysosomal storage disorder", also referred to herein as "lysosomal storage disease" or "LSD", as used herein, preferably refers to genetic diseases and metabolic disorders that result from defects in lysosomal function. Lysosomal storage disorders are caused by lysosomal dysfunction usually as a consequence of deficiency of a single enzyme required for the metabolism of lipids, glycoproteins or so-called mucopolysaccharides. Like other genetic diseases, individuals inherit lysosomal storage diseases from their parents. Although each disorder results from different gene mutations that translate into a deficiency in enzyme activity, they all share a common biochemical characteristic—all lysosomal disorders originate from an abnormal accumulation of substances inside the lysosome.

Farber's disease, also referred to herein preferably as FD, are autosomal recessively inherited genetic diseases which are classified in a subgroup of LSD called lipidoses or lipid storage disorders in which harmful quantities of fatty substances, or lipids, accumulate in the spleen, liver, lungs, bone marrow, and brain.

That FD is inherited in an autosomal recessive pattern means that both copies, or alleles, of the gene must be mutated or altered in such a way that function is impaired, in contrast to a polymorphism, in which the nucleotide sequence is altered but causes no functional disruption, for a person to be affected by the disorder. Most often, the parents of a child with an autosomal recessive disorder are not affected but are carriers of one copy of the altered gene. Such carrier is referred to herein as FD carrier. If both parents are carriers, there is a 25% chance with each pregnancy for an affected child. Genetic counseling and genetic testing is recommended for families who may be carriers of FD.

Mutations in the ASAH1 gene cause complete or partial deficiency of an enzyme called acid ceramidase resulting in accumulation of ceramides and leading to abnormalities in the joints, liver, throat, tissues and central nervous system. Disease onset is typically in early infancy but may occur later in life. Children who have the classic form of Farber disease develop symptoms within the first few weeks of life. These symptoms may include moderately impaired mental ability and problems with swallowing. The liver, heart and kidneys may also be affected. Other symptoms may include vomiting, arthritis, swollen lymph nodes, swollen joints, joint contractures (chronic shortening of muscles or tendons around joints), hoarseness and xanthomas which thicken around joints as the disease progresses. Patients with breathing difficulty may require a breathing tube.

As to prognosis of FD, most children with Farber' disease die by age 2, usually from lung disease. In one of the most severe forms of the disease, an enlarged liver and spleen (hepatosplenomegaly) can be diagnosed soon after birth. Children born with this form of the disease usually die within 6 months.

In accordance with the above forms of Farber's disease it is to be acknowledged that the phenotype of Farber's disease, also referred to as presentations of Farber's disease, may vary significantly. One such phenotype also encompassed by the term Farber's disease in connection with each and any aspect and embodiment of the present invention disclosed herein, is spinal muscular atrophy with progressive myoclonic epilepsy (SMAPME). In connection with said phenotypes it is generally understood in the art that most of them are infantic with the patients typically dying before they reach four years of age. SMAPME, however, is a phenotype of Farber's disease showing a late onset and the patients suffering from such phenotype of Farber's disease may reach adulthood.

As to treatment of FD, there is no specific treatment for Farber' disease. Corticosteroids may be prescribed to relieve pain. Bone marrow transplants may improve granulomas (small masses of inflamed tissue) on patients with little or no lung or nervous system complications. Older patients may have granulomas surgically reduced or removed. These treatments are embodiments of a treatment or a therapy to which it is referred in connection with various aspects and embodiments of the present invention.

Irrespective thereof, the present invention is, in a further aspect, also related to a method for the treatment of a subject suffering from or being at risk of developing Farber's disease, wherein the method comprises
a) performing an assay to detect a biomarker in a sample from the subject;
b) determining the level of the biomarker present in the sample;
c) comparing the level of the biomarker present in the sample to a cut-off value; and
d) treating the subject with a therapy if the level of the biomarker present in the sample is higher than the cut-off value.

In an embodiment of this method for the treatment of a subject according to the present invention, any embodiment of any aspect related to the biomarker and its detection and determination as disclosed herein equally applies.

In a further embodiment, the therapy is selected from the group comprising administration of a corticosteroid to the subject, enzyme replacement therapy and bone marrow transplantation. It will be appreciated by a person skilled in the art that the therapy is selected so as to match to the specific form of Farber's disease from which the subject suffers and, respectively, so as to match to the symptoms deemed to be treated most urgently. The various therapies are used in accordance with common practice.

A further aspect of the present invention is based on both the aspect of the present invention related to the methods for the diagnosis of Farber's disease and the aspect of the present invention related to the method for the treatment of a subject suffering from or being at risk of developing Farber's disease. More specifically, said aspects comprises and, respectively, makes use of the method for the diagnosis of Farber's disease and based on the result of such method, the level of the biomarker present in the sample, the level of the biomarker present in the sample is compared to a cut-off value, and, if the level of the biomarker present in the sample is higher than the cut-off value, a therapy is selected to be applied to the subject. The kind of therapy and the considerations related thereto are similar to the ones disclosed herein in connection with the aspect related to the method for the treatment of a subject suffering from or being at risk of developing Farber's disease, and its various embodiments related thereto.

Ceramides are a family of lipid molecules. A ceramide is composed of sphingosine and a fatty acid. Ceramides are found in high concentrations within the cell membrane of cells. They are one of the component lipids that make up sphingomyelin, one of the major lipids in the lipid bilayer. Ceramides and other sphingolipids found in cell membrane are not purely structural elements, they can participate in a variety of cellular signaling: examples include regulating differentiation, proliferation, and programmed cell death of cells. A typical ceramide has the formula:

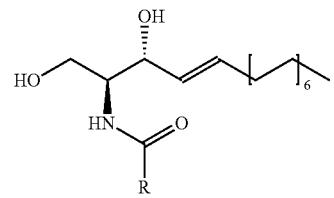

wherein R indicates the alkyl portion of the fatty acid.

In FD the acidic ceramidase enzyme deficiency results in a block of lipid degradation—namely ceramides, resulting in the accumulation of ceramides within lysosomes in the macrophage-monocyte phagocyte lineage. Affected cells become enlarged, and microscopically droplets of lipids can be seen. There is, however, no explanation why C26 ceramide and particularly its cis-isomer is massively accumulating.

C26 ceramide, which is also referred to herein as ceramide C26, is a compound of formula (1):

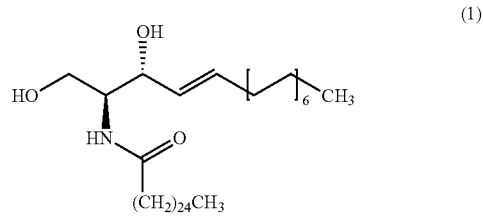

Compound C26 ceramide, which is used as a biomarker according to the present invention can be detected, among others, by the methods disclosed herein. C26 ceramide has a molecular weight of 678, detected as MRM transition in positive mode 679 m/z to 264.4 m/z. Apart from C26 ceramide, medium ceramides as well as long ceramides may be used as a biomarker in the methods and uses of the invention. As preferably used herein, a medium ceramide is a ceramide of formula (2)

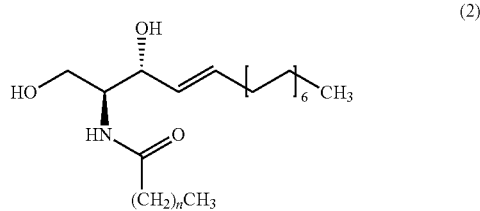

(2)

wherein n is any integer from: 8, 10, 12, 14 and 16.

As preferably used herein, a long ceramide is a ceramide of formula (2), wherein n is any integer from 18, 20 and 22.

The term "sample" as used herein means preferably a limited quantity of a subject's material, wherein said subject's material is part of or has been taken from a subject and/or a subject's body. Preferably, said material is selected from the group comprising body fluids such as blood, a blood product, urine, saliva, cerebrospinal fluid and lymph, as well as stool or any kind of tissue and or cell material being part of a subject and/or a subject's body. It will be acknowledged by a person skilled in the art that the presence of and/or a level of a biomarker of the invention in said sample is intended to be similar to and represent the presence and/or the level of the biomarker in a larger amount of that subject's material. More precisely and as an illustrative, non-limiting example, a level of a biomarker of the invention determined in a sample of, e.g., some ml of blood from a subject also represents a level of said biomarker in the blood of the subject's body. Furthermore, in an embodiment of the method of the invention for diagnosing Farber's disease in a subject, a sample from the subject comprises said subject's material in a form, for example processed, fixed and/or preserved such that said sample is suitable for use in the method of the invention, whereby such processing, fixing and/or preserving preferably does not generate C26 ceramide which was not as such present in the blood of the patient. The subject's material in the sample may thus be diluted, for example with a solvent suitable for the method of the invention such as methanol and/or water, may be dried, for example on a filter card, may be resolved after having been dried such, for example with a solvent suitable for the method of the invention such as methanol and/or water, or a substance may be added, wherein said substance prevents blood from coagulation such as for example EDTA or heparin. It will be further understood by a person skilled in the art that it is within the present invention and its various aspects and embodiments that said subject's material is separated into single components of said subject's material and/or single components of said subject's material are extracted from said subject's material, for example blood is separated into plasma or serum and cellular blood components or protein is precipitated from the sample. Accordingly, in an embodiment of any method according to the present invention wherein the method comprises protein precipitation and/or HPLC, precipitation of protein preferably results in a) a precipitation of cellular blood components and/or protein, more preferably forming a pellet after a step of centrifugation, and b) the biomarker being preferably not precipitated and being present in the supernatant after a step of centrifugation. A person skilled in the art will immediately understand that in an embodiment of any method according to the present invention wherein the method comprises HPLC a supernatant containing the biomarker(s) of the present invention or a part thereof is subjected to HPLC. In connection therewith it is important to understand that the supernatant or a part thereof which is subjected to HPLC comprises the biomarker to be detected as well as, preferably, an internal standard. In an embodiment of the method of the invention wherein an internal standard is added to the sample, the internal standard may be added to the sample before or after a precipitation step, i.e. the internal standard may be added into the sample immediately after the sample is taken from the subject, or may be added to the supernatant which is subjected to HPLC, as well as in between these points in time. A person skilled in the art will know, how and when an internal standard is preferably added to the sample in order to achieve an accurate detection and determination of a level of the biomarker.

It will be immediately understood that after such processing, fixing and/or preserving the sample is subjected to the methods of the invention for detecting and/or determining a or the level of a biomarker contained in said sample, whereby such processing, fixing and/or preserving preferably does not generate C26 ceramide which was not present in the sample from the patient as such.

In an embodiment of the methods of the present invention a sample as used in such methods is prepared from a primary such as whole blood. In an embodiment of the various aspects of the invention the primary sample is whole blood which is, in an embodiment, processed such that it is collected on a dry blood filter card; preferably approximately 4l of full blood are collected on a spot of said dry blood filter card having a diameter of 3 mm. A person skilled in the art will acknowledge that the exact volume thus collected may vary depending on the hematocrit of the specific patient. Accordingly, it is within the ordinary skills of a person of the art that based on the sample taken form the subject and processed, for example into a dried blood spot type sample, the concentration of the biomarker can be determined from said processed sample and, starting therefrom, the concentration of the biomarker in the sample taken from the subject, whereby the sample is preferably a whole blood sample and the processed sample the sample used in and, respectively, subject to the various methods of the present invention as preferably defined by the aspects of the present invention.

As particularly evident from the example part the present invention provides methods for the diagnosis of Farber's disease and biomarkers used in said methods which allow the diagnosis of Farber's disease with high sensitivity and high specificity suitable of clinical application.

The term "Farber's disease status" as used herein, preferably refers to the status of the disease in the subject. Examples of Farber's disease statuses include, but are not limited to, the subject's risk of suffering or developing Farber's disease, the stage of the disease in a subject and the effectiveness of treatment of the disease. Other statuses and degrees of each status are known in the art. In an embodiment of the present invention the Farber's disease status comprises a severe, mild, or healthy Farber's disease status.

The term "diagnosing" as used herein, preferably means determining the presence or the absence of a disease or disorder in a subject and/or determining whether a subject is at risk for developing a disease, a disorder or symptoms related to a disease or disorder as well as predicting a status of a disease. "Diagnosis" or "diagnosing" as used herein also preferably means that a cause of symptoms of a disease which are present or will be present is identified. In connection therewith it is important to note that a person skilled in the art, such as a skilled clinician consulted by a subject suffering from symptoms or suspected to be ill, applies the methods of the present invention or makes the methods of the present invention applied and thus determines whether a subject is at risk for developing a disease, particularly Farber's disease, whether a subject suffers from such disease or predicts the status of such disease, preferably based on the result obtained by the practicing of the methods of the present invention.

Based on said diagnosis the person skilled in the art will recommend to apply, maintain, reduce, elevate or not apply a therapy or to perform further diagnostic tests.

It is thus an embodiment of the method of the present invention for diagnosing Farber's disease that the method comprises giving a recommendation whether a therapy should be applied, maintained, reduced, elevated or not applied.

The term "differentially diagnosing" as used herein in connection with the method of the present invention preferably means that the method allows determining the presence or the absence of a disease or disorder in a subject and/or determining whether a subject is at risk for developing a disease, a disorder or symptoms related to a disease or disorder as well as predicting a status of a disease, wherein the disease is FD.

The term "detecting" in the context of the present invention means methods which include detecting the presence or absence of a substance in a sample and/or qualifying the type of said substance. Detecting can be accomplished by methods known in the art and those further described herein, including, but not limited to, the direct measurement of the affected protein(s) e.g. the sequencing of genes ASAH1 and ASAH2. It will, however, be acknowledged by a person skilled in the art that Farber's disease is characterized only by ASAH1 deficiency. The sequencing of gene ASAH2 is typically performed as a control to eliminate neutral ceramidase deficiency that, in principle, can present the same or very similar symptoms. Any suitable method can be used to detect one or more of the biomarkers described herein. These methods include, without limitation, mass spectrometry such as, e.g. HPLC-MS/MS, fluorescence such as, e.g., sandwich immunoassay, HPLC-fluorescence or HPLC-UV.

A biomarker as used herein, is preferably any biological compound, such as a protein and a fragment thereof, a peptide, a polypeptide, a proteoglycan, a glycoprotein, a lipoprotein, a carbohydrate, a lipid, a nucleic acid, an organic or inorganic chemical, a natural polymer, and a small molecule, which is differentially present in a sample from a subject of one phenotypic status (e.g. having a disease) as compared with another phenotypic status (e.g. not having the disease) and which may be isolated from, or measured in the sample from the subject. In an embodiment of the present invention the biomarker is different from an enzyme, preferably different from a ceramidase and more preferably different from human acid ceramidase. In an alternative embodiment of the present invention the biomarker is an enzyme, preferably a ceramidase and more preferably a human acid ceramidase. Furthermore, the biomarker can be the entire intact molecule, or it can be a portion thereof which is preferably detected by mass spectrometric analysis, an antibody, another protein specifically binding the biomarker, functional nucleic acids specifically binding the biomarker and/or a fluorescent label. A biomarker is furthermore considered to be informative if a measurable aspect of the biomarker is associated with a given status of the patient, such as a particular status of FD. Such a measurable aspect may include, for example, the presence, absence, or the level of the biomarker in the sample from the subject and/or its presence as part of a profile of biomarkers. A profile of biomarkers comprises at least two such measurable aspects, where the measurable aspects can correspond to the same or different classes of biomarkers such as, for example, a nucleic acid and a carbohydrate. A biomarker profile may also comprise at least three, four, five, 10, 20, 30 or more measurable aspects. In one embodiment, a biomarker profile comprises hundreds, or even thousands, of measurable aspects. In another embodiment, the biomarker profile comprises at least one measurable aspect of at least one biomarker and at least one measurable aspect of at least one internal standard.

In an embodiment of any method according to the present invention an internal standard is added to a sample from a or the subject. It will be acknowledged that by said addition of internal standard, also referred to herein as IS, to the sample, i.e. spiking of the sample, to be subjected to such method according to the present invention, the concentration of IS in the sample is known and, e.g., by determining the area under the peak, i.e. the peak area, of the internal standard in, e.g., an HPLC-mass spectrometric chromatogram the relation between a peak area and a concentration of a substance, e.g. of IS, and/or the biomarker of the present invention, i.e. C26 ceramide, is established and thus a means provided for determining the level of the biomarker in the sample. A person skilled in the art will further acknowledge that various molecules may be used as an IS. Nevertheless an IS having a similar chemical structure compared to the molecule such as the biomarker, e.g. a ceramide, is preferable. In a preferred embodiment the molecule being the IS can be distinguished from the biomarker of the present invention, e.g. C26 ceramide, in the methods of the present invention. In a further preferred embodiment the IS is selected such that a molecule which is ideally not present or rare in nature. In accordance therewith, the present inventors have in an embodiment chosen C25 ceramide as an internal standard which is not present as such in nature. C25 ceramide is of the following structure:

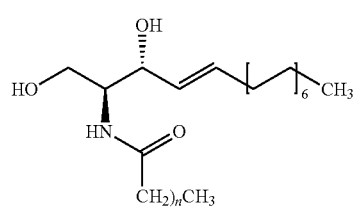

Other compounds which are useful as internal standard in the practicing of the methods of the invention include, but are not limited to, N-lauroyl sphingosine of the following formula

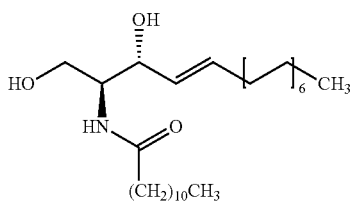

lyso-Gb2 of the following formula

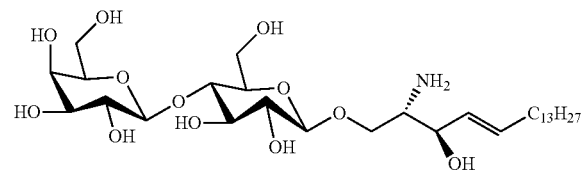

C17 ceramide of the following formula

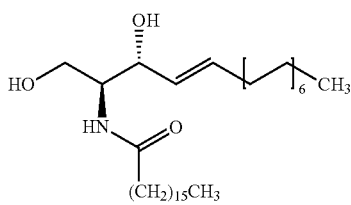

C19 ceramide of the following formula

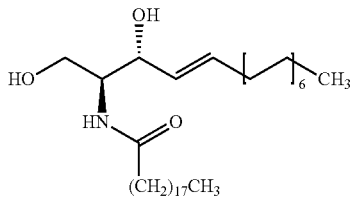

C21 ceramide of the following formula

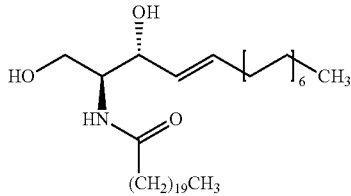

C23 ceramide of the following formula

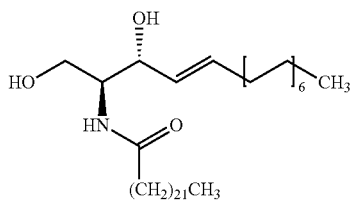

and C27 ceramide of the following formula

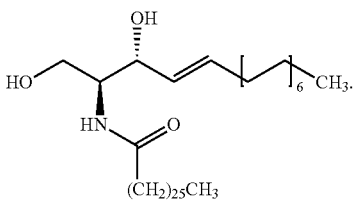

In an embodiment of the various aspects of the present invention where the internal standard is added to a sample from a subject, it is preferred that the IS is added such that it is dissolved in a solvent, e.g. ethanol, prior to said addition to the sample. In a further preferred embodiment that the solvent is selected such that said solvent is capable of causing protein precipitation, preferably is capable of causing the protein precipitation step as subject to the method of the present invention.

In some embodiments of the methods of the present invention a protein precipitation and/or protein precipitation step is part of the methods of the present invention. It will be understood that precipitation as used herein, preferably means the formation of a solid in a solution, i.e. for example the formation of a protein precipitate in a sample, e.g. serum, from a subject. When precipitation, e.g. protein precipitation, occurs in a sample, the solid formed is called the precipitate, or when compacted by a centrifuge, a pellet. The liquid remaining above the solid is in either case called the supernatant. The present invention contemplates different methods of precipitation and/or separating said supernatant and said precipitate or pellet, comprising, among others, settling or sedimentation and centrifugation. A person skilled in the art will know further methods for protein precipitation and/or for separating a supernatant and a protein precipitate, nevertheless said skilled person will acknowledge that if a method, preferably a method of the invention, is applied where precipitated protein will disable a device such as a column or HPLC-column used in connection with the present invention the precipitated protein is preferably separated from the solvent and/or the sample.

In some embodiments of the methods of the present invention a level of a biomarker of the present invention is compared to a level of the same or another biomarker of the present invention determined in another sample, e.g. from the same patient, from another patient, from a control and/or from the same or different points in time, and/or a cut-off value, and/or a level of a control and/or a level of an IS. In connection therewith "comparing" or "compared to" as used herein, preferably means the mathematical comparison of the two or more values of the levels of the biomarker(s). It will thus be immediately evident whether one of said values is higher, lower or identical if at least two of such values are compared with each other.

The term "cut-off value" as used herein preferably refers to a level, concentration and/or a titer of a biomarker of the present invention. In some embodiments where a ratio of two levels, concentrations and/or titers of the biomarkers of the present invention is considered said cut-off value is referred to a value of a ratio to which the ratio of two levels, concentrations and/or titers of the biomarkers is compared, and wherein if said ratio of two levels, concentrations and/or titers of the biomarkers of the present invention determined in the practicing of the methods of the present invention is elevated, increased or higher compared to the cut-off value to which the ratio of two levels, concentrations and/or titers of the biomarkers is compared, this is indicative that the subject is suffering from or is at risk for developing Farber's disease. In one particular embodiment thereof using C26 ceramide as the biomarker allows for diagnosing FD in dried blood spots using a cut-off value for C26 ceramide of 69 nmol/L, preferably 69.0 nmol/L, in case the biomarker is total C26 ceramide, i.e. both or the sum of cis-C26 ceramide and trans-C26 ceramide, and is 28 nmol/L, preferably 28.3 nmol/L, in case the biomarker is cis-C26 ceramide.

It will be appreciated by a person skilled in the art that any cut-off value for a biomarker will vary, at least to a certain extent, whereby such varying depends on the treatment of the sample used in and, respectively, subject to the analysis, the method actually used for determining the level or concentration of the biomarker, i.e. the actually used analysis method, and the instrumentation used in such analysis method. These factors, i.e. the treatment of the sample, the actually used analysis method and the instrumentation used in such analysis method, are also referred to herein as the analytical set-up. In other words, any specific cut-off value is, at least to a certain extent, a function of the analytical set-up actually used.

It is, however, a matter of routine to determine such variation in cut-off values and thus the actual cut-off values for any given analytical set-up in light of the disclosure of the instant application. Insofar, the cut-off value of 69 nmol/L, preferably 69.0 nmol/L, in case the biomarker is total C26 ceramide, and 28 nmol/L, preferably 28.3 nmol/L, in case the biomarker is cis-C26 ceramide, may be used as a reference cut-off value, with the parameters of the analytical set-up used in the determining of the cut-off values for C26 ceramides from blood using LC-MRM-MS preferably being as follows:

LC Parameters
Instrumentation: Ultra Performance Liquid Chromatography device,
 preferably Waters UPLC Aquity
Solvent A: 50 mM formic acid
Solvent B: 50 mM formic acid in Acetone:Acetonitrile 1:1
Column: 3 µm
 preferably C8 column
Flow: 0.9 mL/min
Gradient

| Time (min): | | | | | | |
|---|---|---|---|---|---|---|
| 0.0 | 0.2 | 1.7 | 1.8 | 2.8 | 2.9 | 3.1 |
| % B: 60 | 60 | 100 | 100 | 100 | 40 | 40 |

Column temperature: 60° C.
Equilibration time: 0.1 minutes
MRM-MS Parameters
Instrumentation: Triple quadrupole mass spectrometer
 preferably ABSciex 5500TripleQuad
Scans in period: 118
Relative start time: 0.0
Experiment in period: 1
Scan type: MRM
Polarity: Positive
Ion source: spray, preferably Turbo spray
Resolution Q1: unit
Resolution Q3: unit
MR Pause: 5.000 msec
CAD: 8 psi
CUR: 10 psi
GS1: 45 psi
GS2: 60 psi
IS: 5000 V
TEM: 200° C.
EP: 10 V
Transitions Monitored

| Q1 Mass (Da) | Q1 Mass (Da) | Dwell (msec) | DP (V) | CE (V) | CXP (V) | ID |
|---|---|---|---|---|---|---|
| 664.8 | 264.4 | 200 | 34 | 46 | 13 | A |
| 678.8 | 264.4 | 200 | 34 | 46 | 13 | B |

ID A is C25 ceramide
ID B is C26 ceramide

It will be acknowledged that particularly to the extent the above parameters and details are specific for the indicated instrument and method, respectively, such parameters and details can be adjusted by routine measures which are within the ordinary skills of a person of the art, to any different instrumentation and method. In accordance therewith, the cut-off value of 69 nmol/L, preferably 69.0 nmol/L, in case the biomarker is total C26 ceramide, and 28 nmol/L, preferably 28.3 nmol/L, in case the biomarker is cis-C26 ceramide are also referred to herein as "reference cut-off value".

Additionally, in light of the instant invention according to which it is possible to distinguish a healthy subject from a subject suffering from, or being at risk of suffering from, Farber's disease using total C26 ceramide as defined herein, and/or cis-C26 ceramide as a biomarker, the specific cut-off values based on said total C26 ceramide and said cis-C26 ceramide can be determined for any analytical set-up using, for example, a confidence level of 95% and/or a mean value+2*standard deviation, preferably mean value of the normal controls+2*standard deviation, with the normal controls preferably being healthy subjects. This kind of cut-off values for any analytical set-up, preferably derived from the reference cut-off values disclosed herein, will also be referred to herein as "reference-adjusted cut-off values" or "cut-off value adjusted to the reference cut-off value".

With regard to the impact of the analytical set-up on the cut-off values as set forth herein, the cut-off values for an analytical set-up different from the one used in establishing the reference cut-off values will also be referred to as "adjusted cut-off value" which can be determined as outlined herein.

In an embodiment of each and any aspect of the present invention and any embodiment thereof, any indication as to the level of a biomarker or as to the concentration of a biomarker expressed as "per volume", refers to the level and concentration of the biomarker in the blood of the subject from which a sample has been taken. In accordance therewith, if the concentration of total C26 ceramide is indicated as being more than 69 nmol/L this means that the concentration of the total C26 ceramide, i.e. the sum of the concentration of both cis-C26 ceramide and trans-C26 ceramide, is more than 69 nmol per liter blood of the subject from which the sample has been taken, which is indicative that the subject is suffering from Farber's disease; conversely, if the total C26 ceramide is below 69 nmol/L, this is indicative that the subject from which the sample has been taken is a healthy subject not suffering from Farber's disease.

Similarly, if the concentration of cis-C26 ceramide is indicated as being more than 28.3 nmol/L this means that the concentration of cis-C26 ceramide is more than 69 nmol per liter blood of the subject from which the sample has been taken, which is indicative that the subject is suffering from Farber's disease; conversely, if the cis-C26 ceramide is below 28.3 nmol/L, this is indicative that the subject from which the sample has been taken is a healthy subject not suffering from Farber's disease.

In some embodiments of the methods of the present invention the level of the biomarker is also determined in a control. As used herein, a control is preferably a sample from a subject, wherein the Farber's disease status of said subject is known. In an embodiment a control is a sample of a healthy patient. In a further embodiment an amount of said biomarker is added to said sample of a healthy patient prior to determining the level of said biomarker in said sample of a healthy patient comprising said added biomarker, preferably in the practicing of a method of the present invention. In a further embodiment the control is a sample from at least one subject having a known Farber's disease status, e.g. a control patient, and in a still further preferred embodiment also comprises the genetic status with regard to mutations of the gene, affected in said disease, comprising ASAH1, i.e. comprising the subject having homozygous and/or compound heterozygous mutations, the subject being a carrier of a mutation. In a further preferred embodiment the control is a sample from a subject not being treated for Farber's disease. In a still further preferred embodiment the control is a sample from a single subject or a pool of samples from different subjects and/or samples taken from the subject(s) at different points in time.

The term "level" or "level of a biomarker" as used herein, preferably means the concentration of a substance and/or titer of a substance, preferably of a biomarker of the invention and more preferably of C26 ceramide, within a sample of a subject. It will be understood by a skilled person that in certain embodiments of the methods of the invention said sample is used as such in the practicing of said methods. It is, however, also within the present invention that said sample is subject to processing prior or during its use in the methods of the present invention. In an embodiment said sample may be subjected, e.g., to a step of protein precipitation, separation, e.g., centrifugation and/or HPLC and subsequently subjected to a step of determining the level of the biomarker, e.g., using mass spectrometric analysis. It should be further noted that whenever the term "a" level of a biomarker is used in connection with a level of the biomarker of the invention which is to be determined according to or in the practicing of the present invention, "the" level of the biomarker of the present invention which is to be determined by the methods of to the present invention and which is contained in the sample subjected to the method(s) of the invention is meant.

The level of a biomarker is different between different statuses of Farber's disease, if the mean or median level of the biomarker in the different groups is calculated to be statistically significant. Biomarkers, alone or in combination, provide measures of relative risk that a subject belongs to one phenotypic status or another. Therefore, a biomarker of the present invention is useful in an embodiment of the present invention as markers for disease, or for therapeutic effectiveness of a drug or a treatment.

The term "determining the level" of a biomarker as used herein, preferably means methods which include quantifying an amount of at least one substance in a sample from a subject and/or quantifying an amount of said substance contained in a part of the body of the subject, such as saliva, blood, lymph, serum, plasma or liquor and/or quantifying an amount of said substance in the subject, preferably the substance being selected from the group comprising a biomarker.

It will be understood by a person skilled in the art that detecting and/or determining the level of C26 ceramide in a sample from the subject, not chemically converted, transformed or derivatized. In a further preferred embodiment a step of detecting and/or determining the level of a biomarker in a sample from the subject, wherein the biomarker is C26 ceramide, is performed subsequent to separation using HPLC by application of mass spectrometric analysis.

A subject is considered to be a healthy subject with regard to Farber's disease, if the subject does not suffer from one or more than one symptoms associated with Farber's disease. In an embodiment of the methods of the invention a subject will be considered to be healthy regarding Farber's disease, if it has no mutation of the functional parts of the ASAH1 gene resulting in a reduction of or deficiency of the respective protein or the activity thereof, resulting in one or more than one symptoms associated with FD.

In connection therewith it is important to understand that such patient being a carrier of a mutation as outlined above is not considered to be a healthy subject within the meaning of the present invention although said carrier may not suffer from symptoms associated with Farber's disease. In certain embodiments of the methods of the present invention Farber's disease also comprises FD carrier. In an embodiment of each and any aspect of the present invention the specificity of the biomarker is about 83%, wherein preferably the biomarker is C26 ceramide. It is important to note that the methods of the invention are equally suitable to identify a FD carrier. The methods of the present invention are suitable to diagnose whether or whether not a subject is a FD carrier. The method of the present invention is further suitable for differentiating, diagnosing and/or differentially diagnosing whether a subject is healthy, is a FD carrier or is a FD patient. In an embodiment of these methods of the invention the specificity of the biomarker is about 83%, wherein preferably the biomarker is C26 ceramide.

Said mutations, i.e. mutations of ASAH1, Will be detected if a sample from the subject is subjected to a genetic testing for such mutations as described herein. In a further embodiment of the present invention a sample from a healthy subject is used as a control sample or as a blank matrix in the methods of the present invention. A blank matrix as used herein is preferably a sample from a healthy subject. Nevertheless, it will be understood that such a blank matrix may contain a native level of C26 biomarker.

In an embodiment of the present invention the level of a biomarker is indicative for the subject for suffering from or for being at risk for developing a disease or disorder, preferably Farber's disease. The level of the biomarker determined in accordance with the present invention is compared to a control level of the biomarker, wherein the result of said comparison allows for diagnosing a disease, preferably Farber's disease.

More specifically, comparing the level of the biomarker in the sample from the subject to the control level of the biomarker comprises comparing the level of the biomarker in the sample from the subject to a cut-off value, wherein if a level of the biomarker in the sample from the subject is elevated, increased or higher compared to the cut-off value, this is indicative that the subject is suffering from or is at risk for developing FD or is a FD carrier; and/or wherein if a level of the biomarker in the sample from the subject is decreased or lower compared to the cut-off value this is indicative that the subject is not suffering from or is not at risk for developing FD disease.

The term "being at risk for developing a disease" as used herein preferably means that it is likely that a subject will suffer from said disease and/or will develop said disease or symptoms associated with said disease, particularly if no treatment is applied. In connection therewith it has to be acknowledged that LSDs are genetic disorders and thus the occurrence of relatives, particularly parents having said disease or having a mutation known to be the cause of said disease are indicative for a subject, e.g. the child of two FD patients or two FD carriers, to be at risk for developing said disease. It will be furthermore acknowledged that the progression of a disease is linked to the occurrence of symptoms as well as the severity of said symptoms. Accordingly, a person not suffering from symptoms at present, however, may be at risk for developing the disease, for example, because although genetically mutations of a gene, known to cause a disease are present, no symptoms or no severe symptoms occur. Nevertheless, it will be immediately understood that the methods and biomarkers of the present invention, particularly if the level of said biomarker according to the present invention is elevated, allow for diagnosing that such subject is at risk for developing the disease independent from the presence or absence of symptoms. Accordingly, the methods according to the present invention allow for determining whether a subject is at risk of suffering from Farber's disease. It is also within the present invention that a therapy is applied, maintained, reduced, elevated or not applied based on whether the subject is at risk of suffering from Farber's disease or not.

It is also within the present invention that comparing the level of the biomarker in the sample from the subject to a control level allows for determining the severity of Farber's disease, wherein if a level of the biomarker in the sample from the subject is elevated, increased or higher compared to the control level that is indicative that the subject is suffering from or is at risk for developing Farber's disease of a more severe status or progression; and wherein if a level of the biomarker in the sample from the subject is decreased or lower compared to the control level that is indicative that the subject is suffering from or is at risk for developing Farber's disease of a less severe status or progression. In a further embodiment of the present invention that comparing the level of the biomarker in the sample from the subject to the control level comprises comparing a level of the biomarker in said subject to a level of the biomarker detected in a sample from a control, wherein if a level of the biomarker in the sample from the subject is elevated, increased or higher compared to the control sample this is indicative that the subject is suffering from and/or is at risk for developing Farber's disease; and/or a level of the biomarker in the sample from the subject is elevated, increased or higher compared to the control sample this is indicative that the subject is suffering from or is at risk for developing Farber's disease of a more severe status or progression. Said control preferably is selected from the group comprising healthy subjects, subjects suffering from Farber's disease or being at risk of suffering from Farber's disease symptoms, subjects being positively tested for a mutation or a combination of mutations of the gene ASAH1. In a further embodiment of the present invention a control level is determined in a sample from a control, wherein optionally C26 ceramide is added to the sample from the control in a specific quantity prior to determining the level of C26 ceramide in the sample from the control.

It is the merit of the present inventors that a method for diagnosing Farber's disease in a subject could be established wherein the method comprises detecting a biomarker in a sample from a subject, wherein, preferably, the biomarker is C26 ceramide, preferably further comprising determining a level of the biomarker in the sample from the subject, and more preferably further comprising comparing the level of the biomarker in the sample from the subject to a cut-off value, which shows high sensitivity. In other words, the sensitivity, which means the proportion of actual positives which are correctly identified as such, is high, which means that the percentage of Farber's disease patients correctly identified as having the disease is as high as has been outlined above. In contrast, in a statistic test as described herein specificity means the proportion of negatives which are correctly identified as negatives, in other words the percentage of healthy patients correctly identified as not having Farber's disease. A person skilled in the art will acknowledge that thus an optimal prediction of a diagnostic test such as in some embodiments of the methods according to the present invention in general aims to achieve 100% sensitivity, i.e. predict all patients having a disease, such as Farber's disease or being at risk of suffering from said disease, as having the disease or being at risk from suffering from said disease, respectively.

In an embodiment of the methods according to the present invention a specificity of at least 80%, to 100% is preferred. In a further embodiment of the present invention of the methods according to the present invention the methods allow for diagnosing Farber's disease in a subject independent from a progression status of Farber's disease in the subject. More specifically, the methods of the present invention allow for diagnosing Farber's disease in a subject having an early status of Farber's disease as well as in a subject having an advanced or progressed status of Farber's disease.

A person skilled in the art will acknowledge that although the specificity and/or the sensitivity of the methods according to the present invention are as high as described above and were determined as described in the examples hereinafter, individual cases may not be excluded where a patient having Farber's disease will be tested false negative or where a patient not having Farber's disease will be tested false positive with a method of the invention. A person skilled in the art will thus immediately acknowledge that according to the methods according to the present invention, wherein a level of a biomarker is compared to a cut-off value, such comparison to said cut-off value is for use to differentially diagnose a disease and/or from a level and/or a value in a healthy subject. Having said this, it is obvious for the person skilled in the art that also according to the methods of the present invention, wherein the method is for diagnosing FD patient and carrier, individual cases may not be excluded where a patient having FD will be tested false negative or where a patient not having FD will be tested false positive, or where the type and/or status is diagnosed incorrectly with a method of the invention.

Therefore, it is important to note that although the sensitivity and the specificity of the method of the present invention may vary if patient collectives other than the one reported in the Example part, e.g. varying in number of patients, will be subject to the methods of the present invention, it is the firm belief of the inventors that no method known in the prior art, especially using biomarkers, will achieve a higher specificity and a higher sensitivity compared to the methods according to the present invention. This is especially true since the limit of detection of the methods of the present invention allows for determining the level of C26 ceramide in healthy subjects.

A "limit of detection" of a substance such as C26 ceramide, as used herein, preferably is a level of the substance determined by a method for determining a level of the substance, wherein a level less then or lower then said limit of detection cannot be determined by said method. It is thus immediately clear that a "cut-off value" and a "limit of detection", as used herein, are preferably not necessarily identical, although both reflect a certain level of a substance, e.g. of a biomarker of the present invention, i.e. C26 ceramide. It will be immediately understood that a cut-off value will be selected preferably such that selectivity and sensitivity of the method are as high as possible. In contrast thereto a limit of detection represents an absolute level of the biomarker of the present invention which reflects the minimum level of biomarker which can be detected with a method for determining the level of said biomarker. It is thus immediately clear that a limit of detection depends on the method for determining a level of a substance and on the substance the level of which is to be determined by the method. A skilled person will immediately understand that a high limit of detection, e.g. higher than an ideal cut-off value would possibly result in a low sensitivity of the method since the percentage of true positives that are predicted by a test to be positive also depends on whether a level of the biomarker may be determined for said true positives. In other words, if the limit of detection is higher than an ideal cut-off value, true positives having a level of the biomarker slightly higher than the cut-off value may not be distinguished from true negatives having a level of the biomarker lower than the cut-off value since no level of the biomarker may be determined for both true positives having a level of the biomarker slightly higher than the cut-off value and negatives having a level of the biomarker lower than the cut-off value. It is thus immediately clear that a low limit of detection is of advantage. It is therefore also the merit of the inventors to show that a lower limit of detection allows for a method for diagnosing Farber's disease in a subject comprising a step of determining a level of a biomarker present in the sample with higher selectivity and sensitivity. An "ideal cut-off value" as used herein, preferably is the cut-off value as described herein, wherein the method using said ideal cut-off value has the highest selectivity and sensitivity.

In an embodiment of the methods according to the present invention the methods comprise a step of validating said method by diagnosing a disease or disorder, preferably Farber's disease in a subject by the method of the present invention; a step of diagnosing the disease or disorder, preferably Farber's disease, in a subject by a genetic testing, comprising sequencing of a gene, preferably sequencing of a gene a mutation of which is known to the one skilled in the art to cause the disease or disorder, more preferably sequencing the ASAH1 gene; and comparing the results of said method and said genetic testing. A healthy subject as used herein, preferably is considered to be healthy with regard to a disease or disorder if said subject is not suffering from symptoms associated with said disease or disorder and if the result of a genetic testing reveals no mutations of a gene a mutation of which is known to the one skilled in the art to cause the disease or disorder. A healthy subject also is understood to be a subject being positively tested for not having Farber's disease. In a preferred embodiment a healthy subject is a subject not being a carrier of FD.

The term "qualifying Farber's disease status" in a subject as used herein, preferably means a classification of a subject's biomarker profile selected from the group comprising to identify or detect the presence or absence of Farber's disease in the subject, to predict the onset of or the risk for developing of Farber's disease in the subject, to determine the course of Farber's disease in a subject, to determine and/or predict the severity of Farber's disease in a subject, to determine whether a subject suffers from an early status of Farber's disease or an advanced or progressed status of Farber's disease or to determine whether a level of a biomarker in a subject has significantly changed over time.

The term "managing subject treatment" or "subject management" as used herein, preferably refers to the behavior of the clinician or physician subsequent to the determination of Farber's disease status. For example, if the result of the methods according to the present invention is inconclusive or there is reason that confirmation of status is necessary, the physician may order new tests, such as testing for the function of the affected proteins and/or sequencing of the ASAH1 gene. Alternatively, if the status indicates that treating for Farber's disease is appropriate, the physician may schedule the subject for treating for Farber's disease. Likewise, if the status is negative or if the results show that treatment has been successful, no further management may be necessary. Nevertheless a person skilled in the art will immediately acknowledge that besides gene therapy any suitable and/or effective therapy may be applied. Furthermore it is an embodiment of the present invention that managing subject treatment comprises titrating of a dose of a drug applied as a treatment for Farber's disease, e.g. units of recombinant enzyme applied in enzyme replacement therapy (ERT), administered to a patient. In some embodiments of the methods of the present invention wherein a level of a biomarker present in a sample from a subject is determined at several points in time, or is compared to other levels of the biomarker, a cut-off value and/or a level of said biomarker in a control and/or another value of a ratio of the levels of two biomarkers, a skilled person will apply or not apply a therapy, or amend a therapy already applied in order to treat or not to treat, or to continue treating Farber's disease.

It is within the present invention that a skilled person will apply a dosage and/or maintain a dosage or amend a dosage, e.g. apply a dosage or a higher dosage, i.e. elevate a dosage, if such a comparison of the level of a biomarker e.g. that the level of said biomarker is higher than for example, a cut-off value, i.e. the patient is diagnosed to have Farber's disease; or that a level determined in the same patient earlier in time is lower or the same, i.e. a therapy applied is not sufficient, i.e. does not result in a decrease in the level of the biomarker. On the other hand, a skilled person will apply or not apply a dosage or maintain or reduce a dosage, e.g. apply no dosage or a lower dosage, i.e. decrease a dosage, if such a comparison of the level shows e.g. that the level of said biomarker is lower than for example, a cut-off value, i.e. the patient is diagnosed not to have Farber's disease; or that a level determined in the same patient earlier in time is higher, i.e. a therapy applied is sufficient, i.e. does result in a decrease in the level of the biomarker. Nevertheless, it will also be immediately understood that a skilled person will consider a patient's history, i.e. a skilled person managing treatment of a patient suffering from Farber's disease and being treated such that a level of biomarker is lower than a cut-off value, for example, will not decide to stop treatment rather than decrease a dosage and increase the time between further applications of the methods of the present invention.

The course of Farber's disease may be determined by the method according to the present invention by determining a level of the biomarker in the sample from the subject at different points in time in the course of the disease. It is important to note that a single application of a method for diagnosing Farber's disease according to the present invention allows for diagnosing Farber's disease and in certain embodiments comprises a step of managing subject treatment based on the diagnosis of whether the subject is suffering from or is at risk for developing Farber's disease. If a subject a sample of whom is thus subjected to the method of the present invention, is tested positive for suffering from or being at risk for developing Farber's disease a skilled clinician will know how to decide concerning managing subject treatment. It will be immediately understood that independent of the decision of a skilled clinician on how to manage subject treatment the skilled clinician may decide for at least one additional application of the method according to the present invention at a later point in time.

It is thus an embodiment of the present invention that the levels of the biomarker are determined at the different points in time, wherein different points in time means at least two points in time, may be compared. The same is also true for the wording "at several points in time" which means that there are two or more points in time; in a preferred embodiment such two or more points in time are timewise separated such that any effect of a measure taken may become detectable, for example, a change in one or more symptoms of Farber's disease upon administration of a drug, whereby, preferably such change may be a qualitative change or a quantitative change. The time difference between such different points in time or several points in time can be determined by a person skilled in the art using routine consideration or can be determined by routine test procedure. Without wishing to be bound by any theory the present inventors have found that the level of the biomarker of the present invention in samples form one particular patient may be correlated to the severity of the disease in said patient at the point in time the sample from the patient is taken. It will thus immediately be understood that an elevated level of the biomarker determined in the sample of a later point in time compared to the level of the biomarker determined in the sample of an earlier point in time is indicative for a more severe status of the subject at the later point in time compared to the status of the subject at the earlier point in time. A decreased level of the biomarker and/or ratio of the levels of two biomarkers determined in the sample of a later point in time compared to the level of the biomarker determined in the sample of an earlier point in time is indicative for a less severe status of the subject at the later point in time compared to the status of the subject at the earlier point in time. Accordingly, in one aspect the present invention provides a method for determining the course of Farber's disease in a subject comprising the step of determining at several points in time a level of a biomarker present in a sample from the subject, wherein the biomarker is C26 ceramide. In a further aspect the invention concerns a method for determining the effectiveness of at least one treatment applied to a subject being positively tested for suffering from or being at risk for developing Farber's disease comprising the step of determining at several points in time a level of a biomarker present in a sample from the subject, wherein the biomarker is C26 ceramide. It will be immediately understood by a person skilled in the art that the methods of the present invention thus allow for selecting a therapy and/or adjusting the doses and/or dosage of a selected therapy based on the results of the method of the invention. If, for example, the subject is scheduled for treatment for Farber's disease the method for diagnosing Farber's disease in a subject according to the present invention may be applied every 3 months and levels of the biomarker thus determined will be compared in order to determine the effectiveness of the treatment(s) and/or therapy/therapies applied to the subject. If the subject reaches a status, wherein a stable level of the biomarker is maintained over time the frequency of application of the method for diagnosing Farber's disease in a subject according to the present invention may be reduced to every 6 month. If the dosage of the therapy is changed, e.g. the units of recombinant enzyme applied in ERT are reduced or increased, the frequency of application of the method for diagnosing Farber's disease in a subject according to the present invention may be set back to every 3 month. By comparison of the determined levels of the biomarker in the samples from the subject the skilled physician will recognize whether the level of the biomarker increases, decreases or whether a stable level of the biomarker is maintained over time. Accordingly, the skilled physician may decide to reduce the dosage of the therapy, e.g. the units of recombinant enzyme applied in ERT; to increase the dosage of the therapy; or to maintain the dosage of the therapy according to the comparison of the levels of the biomarker with the method according to the present invention.

A person skilled in the art thus will acknowledge that the progression, i.e. course of Farber's disease, as well as the effectiveness of a therapy in a single subject can be monitored by frequent determining of the level of C26 ceramide in samples from the subject.

In a further aspect the invention concerns a method for determining the effectiveness of at least one treatment applied to a subject being positively tested for suffering from or being at risk for developing Farber's disease, wherein the method comprises the step of determining at several points in time a level of a biomarker present in a sample from the subject, wherein the biomarker is C26 ceramide. In connection with what has been outlined above in relation to managing subject treatment a person skilled in the art will immediately understand that the effectiveness of one treatment or the combination of at least two treatments may be compared by applying the methods of the present invention. Thus, it is possible to test and compare several new drugs, dosage forms, dosages or treatments for Farber's disease by the method of the present invention.

It is an embodiment of the present invention that the method for diagnosing Farber's disease according to the present invention is independent of whether the subject has or has not been previously treated for Farber's disease. In accordance therewith, the sample from the subject may be a sample from a subject who has been previously treated for Farber's disease as well as a sample from a subject who has not been previously treated for Farber's disease. It is thus a further embodiment of the present invention that the methods of the present invention comprise a step of managing subject treatment and/or determining a level of the biomarker in the sample from the subject after subject management. Said subject treatment can be based on the diagnosis of whether the subject is suffering from or is at risk for developing Farber's disease; on the detection of the biomarker in a sample from the subject after subject management; or on the determining of the level of the biomarker in the sample from the subject after subject management, with the biomarker being C26 ceramide. Nevertheless, a person skilled in the art will understand that a sample of some patients not having Farber's disease or of some patients being successfully treated for Farber's disease will show a level of C26 ceramide lower than the limit of detection.

Without wishing to be bound by any theory the present inventors assume that the level C26 ceramide present in a sample from a subject further correlates with the severity of the disease in a subject suffering from Farber's disease. In connection therewith the present inventors assume that although, in principle, the level of C26 ceramide is different in particular individuals, and more specifically may be different in particular individuals having the same mutation (s), that the higher is a level of C26 ceramide, the higher is the severity of a course of Farber's disease in terms of a statistical mean according to a clinical score. Thereby the level of C26 ceramide correlates with the severity of Farber's disease in that in patients being positively tested for distinct mutations of the ASAH1 gene, being known to generally causes a mild or a more severe course of Farber's disease, a level of C26 ceramides, determined in said patients statistically correlates with the severity generally related to such mutation.

Thus a further aspect of the present invention concerns a method for determining the severity of Farber's disease in a subject comprising
a) a step of determining a level of the biomarker present in a sample from the subject wherein the biomarker is C26 ceramide and
b) a step of determining the severity of Farber's disease, e.g. by comparing the level of C26 ceramide in a subject preferably determined by a method of the present invention to a clinical score.

In connection therewith it is important to note that if a level of C26 ceramide is determined in samples from the patients suffering from Farber's disease showing a mutation usually linked to a more severe course of Farber's disease upon sequencing of the respective gene (homozygous and compound heterozygous) subjected to a method of the present invention, a mean-level of C26 ceramide is higher than the mean-level C26 ceramide determined in samples from the patients suffering from Farber's disease showing a mutation usually linked to a milder course of Farber's disease upon sequencing of the respective gene, applying the same method. In other words, the level of the biomarker will be correlated with the severity of the disease and subsequently with the type of mutation in the ASAH1 gene. A "mutation usually linked to a more severe course of Farber's disease" as used herein preferably is known to cause a more severe course of Farber's disease—this is especially true in case the subject is homozygous as to said mutation. Corresponding to that in an embodiment a higher mean-level of C26 ceramide is determined in the homozygous compared to the homozygous mutation usually linked to a milder course of Farber's disease. Moreover, patients having a compound heterozygous usually linked to a more severe course of Farber's disease have a significant lower C26 ceramide than homozygous ones. A person skilled in the art will know clinical scores to categorize the severity of Farber's disease or symptoms or an group of symptoms thereof. It is thus an embodiment of the method of the present invention that the course of Farber's disease in a patient is predicted and more particularly the severity of Farber's disease is determined based on the level of the biomarker determined according to the method of the present invention.

A person skilled in the art will acknowledge that a level of the biomarker of the present invention determined in a sample from a subject wherein said level of the biomarker is correlated with the severity of Farber's disease as described above, will be indicative for applying a certain therapy and/or dose or dosage of said therapy. For example, if the level of the biomarker determined according to the methods of the invention is correlated with "severe" Farber's disease status the subject is scheduled for treatment of Farber's disease and the method for diagnosing Farber's disease in a subject according to the present invention may be applied every 3 months and levels of the biomarker thus determined will be compared in order to determine the effectiveness of the treatment(s) and/or therapy/therapies applied to the subject. If the subject reaches a status where the level of the biomarker is correlated with a "mild" Farber's disease or wherein a stable level of the biomarker is maintained over time, the frequency of application of the method for diagnosing Farber's disease in a subject according to the present invention may be reduced to every 6 month.

In another aspect the present invention is related to a method of determining the effectiveness of a composition for the treatment of Farber's disease. Such method may comprise the steps of determining a level of C26 ceramide in a subject having Farber's disease; administering to said subject said compound in an amount sufficient to determine the effectiveness of said compound; re-determining the level of C26 ceramide in said subject; comparing the level of C26 ceramide determined before and after administering said composition, wherein a lower level of C26 ceramide determined after administering said composition compared to the level of C26 ceramide determined prior to administering said composition indicates the effectiveness of said compound for treating Farber's disease.

Farber's disease affects mostly children and they often die at a young and unpredictable age, many within a few months or years of birth. Many other children die of this disease following years of suffering from various symptoms of their disorder.

It is the merit of the present inventors having found that the biomarkers of the present invention and C26 ceramide in particular are/is useful for the diagnosis of Farber's disease in a subject independent from the age of the subject. It is thus an embodiment of the present invention that the method of the present invention allows for diagnosing Farber's disease in a subject independent from age. In a preferred embodiment the method of the present invention the subject is a subject of young age. A subject of young age as used herein preferably is a subject of less than 30 years of age, more preferably of less than 20 years of age and most preferably of less than 10 years of age. In an embodiment of the method of the invention, the subject is a subject suffering from any one of type 1 of Farber's disease, type 2 of Farber's disease, type 3 of Farber's disease, type 4 of Farber's disease, type 5 of Farber's disease, type 6 of Farber's disease or type 7 of Farber's disease. The above disclosure as to the characteristics of a subject equally apply to any aspect of the instant invention and thus to any method disclosed herein. In other words, the subject of any method of the invention may be a subject suffering from any one of type 1 of Farber's disease, type 2 of Farber's disease, type 3 of Farber's disease, type 4 of Farber's disease, type 5 of Farber's disease, type 6 of Farber's disease or type 7 of Farber's disease.

As preferably used herein, a Farber patient is a subject suffering from Farber's disease.

As preferably used herein, a Farber sample is a sample taken form a Farber patient; preferably the sample is a blood sample or a derivative thereof such as a dried blood sample, a serum sample or a blood sample.

As preferably used herein in connection with each and any aspect of the invention and each and any embodiment of the present invention, any indication of a level or concentration of a compound referring to a volume unit is meant to refer to a volume unit of a sample, more preferably of the sample in which said compound is contained with the indicated level of concentration.

It will be appreciated by a person skilled in the art that the sequence of the individual steps of the methods of the present invention may differ from the specific sequence indicated herein. Such change in sequence, however, is only possible where the intended purpose of the method is still achieved despite such change in sequence of the individual steps.

It will also be appreciated by a person skilled in the art that if in any method of the present invention as subject to the various aspects and embodiments disclosed herein a comparison is made and it is indicated that a first level of a compound such as a biomarker is lower than a second level of the compound, preferably such lower level is significantly lower, more, preferably not because of errors in the detection and/or quantification of the compound, most preferably such lower level goes along with a change in one or more symptoms of Farber's disease or one or more clinical, biochemical or physiological parameters characteristic for or associated with Farber's diseases.

The kit according to the present invention contains an interaction partner of the biomarker, whereby such interaction partner is a compound which interacts with the biomarker, whereby, preferably, the biomarker is cis-C26 ceramide, trans-C26 ceramide or both cis-C26 ceramide and trans-C26 ceramide. It is within the present invention that the interaction partner is a mixture of an interaction partner interacting with cis-C26 ceramide and an interaction partner interacting with trans-C26 ceramide. As preferably used herein interacting means that said interaction partner binds to the biomarker, whereby such binding may be through non-covalent binding or covalent binding, preferably non-covalent binding. The reaction conditions under which such binding occurs depend on the particular interaction partner and reaction conditions, and can be determined by a person skilled in the art by means of routine experimentation.

In an embodiment the kit according to the present invention contains a capture agent, whereby such capture agent, whereby such capture agent, is a compound which interacts with the biomarker, whereby, preferably, the biomarker is cis-C26 ceramide, trans-C26 ceramide or both cis-C26 ceramide and trans-C26 ceramide. It is within the present invention that the capture agent is a mixture of a capture agent interacting with cis-C26 ceramide and a capture agent interacting with trans-C26 ceramide. As preferably used herein interacting means that said capture agent binds to the biomarker, whereby such binding may be through non-covalent binding or covalent binding, preferably non-covalent binding. The reaction conditions under which such binding occurs depend on the particular capture agent and reaction conditions, and can be determined by a person skilled in the art by means of routine experimentation.

A preferred interaction partner is one selected from the group comprising a target binding protein, a target binding peptide, an anti-target antibody or antigen-binding fragment thereof, an anticalin binding to the target, an aptamer binding to the target, and a spiegelmer binding to the target, with the target being as defined above.

A preferred capture agent is one selected from the group comprising a target binding protein, a target binding peptide, an anti-target antibody or antigen-binding fragment thereof, an anticalin binding to the target, an aptamer binding to the target, and a spiegelmer binding to the target, with the target being as defined above.

As preferably used herein, in an embodiment the peptide is a polymer comprising a chain of amino acid covalently linked through a peptide bond, whereby the polymer comprises less than 100 amino acid residues. As used herein, the term peptide comprises also polypeptides typically comprising from about 10 to about 100 amino acid residues, and peptide in the narrower sense typically comprising 2 to about 10 amino acid residues. In accordance therewith, a protein is a polymer comprising more than 100 amino acid residues.

A target binding protein is, in an embodiment, a target binding anticalin. Anticalins a target binding polypeptides which are, among others, described in German patent application DE 197 42 706.

Methods for the generation of an antibody binding to a distinct target, are known in the art, and, for example, described in Harlow, E., and Lane, D., "Antibodies: A Laboratory Manual," Cold Spring Harbor Laboratory, Cold Spring Harbor, N.Y., (1988).

Aptamers are D-nucleic acids which are either single stranded or double stranded and which specifically interact with a target molecule, preferably through a mechanism different from Wartson-Crick base pairing. The manufacture or selection of aptamers is, e. g., described in European patent EP 0 533 838.

Spiegelmers are L-nucleic acids which are either single stranded or double stranded and which specifically interact with a target molecule, preferably through a mechanism different from Wartson-Crick base pairing. The manufacture or selection of spiegelmers is, e.g., described in international patent application WO 98/08856.

All of the methods disclosed in connection with the various aspects of the invention as to the diagnosis of Farber's disease may be equally used for each and any other aspect of the present invention and any of its embodiments thereof, including, but not limited to the method for determining the effectiveness of at least one treatment, the method for determining the effectiveness of a compound for treatment of Farber's disease, the method for determining the course of Farber's disease, the method of prognosis of Farber's disease, the method for the treatment of Farber's diseases, the use of mass spectrometric analysis for the detection of a biomarker, the use of a biomarker for the diagnosis of Farber's disease, and the kit.

Furthermore, each embodiment of one aspect of the present invention disclosed herein is also an embodiment of each and any of the other aspects of the present invention disclosed herein.

The present invention is now further illustrated by the following figures and examples from which further features, embodiments and advantages may be taken.

More specifically,

Figure 8:
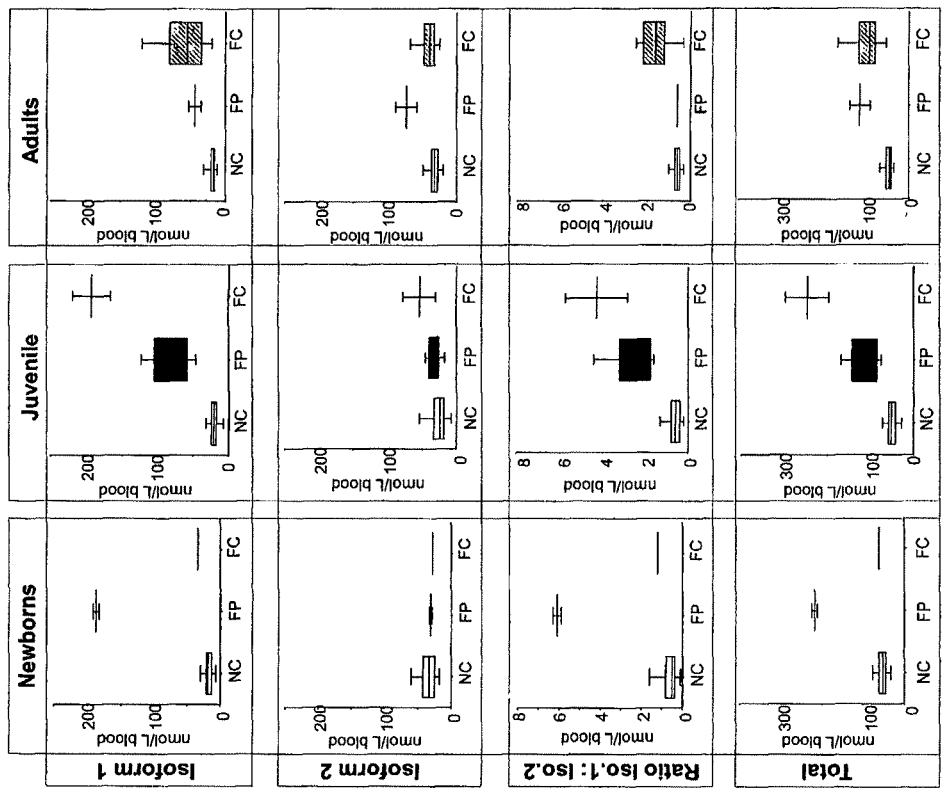
Figure 9:
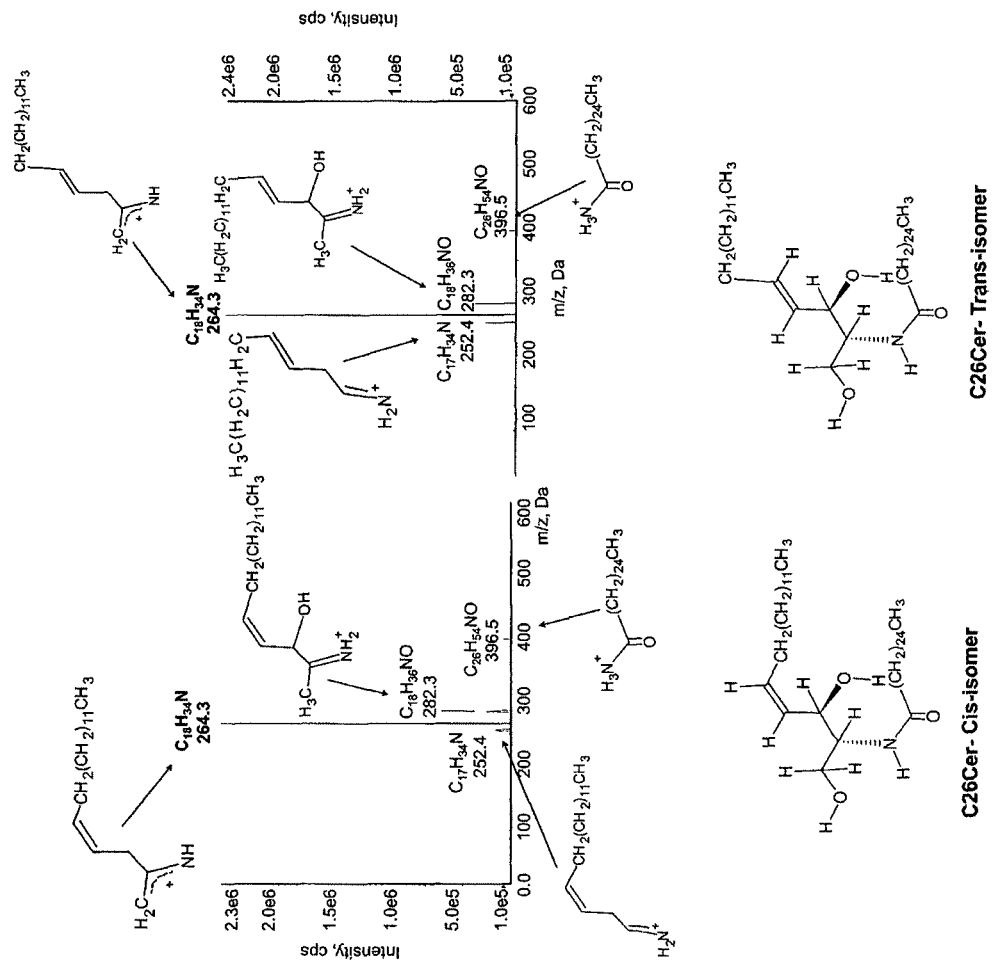

FIG. 8 is a total ion chromatogram (TIC) profile of C26-ceramide isoforms in samples from genetically confirmed Farber patients (Farber patient) vs normal controls (Healthy control), whereby the isoforms were analyzed from were dried blood spots (A) or from in clear plasma (B); and FIG. 9 is a fragmentation pattern of the two isoforms of Ceramide C26 separated by LC/MS using real tandom mass spectrum (MS/MS).

EXAMPLES

In the Examples described in the following DBS was used as a sample from a subject. Nevertheless, a person skilled in the art will acknowledge that depending on the used type of sample from a subject, e.g. comprising saliva, liquor, plasma, serum, full blood, blood on a dry blood filter card or another blood product, the method of the present invention has to be adjusted to the type of sample and furthermore a cut-off value has to be determined for each type of sample according to the method described in the following examples.

Example 1: Method for the Detection of C26 Ceramide in DBS

Equipment

For detecting C26 ceramide and/or a substance with molecular weight of 678, detected as MRM transition in positive mode 679 m/z to 264 m/z, in a sample of plasma from a subject the following equipment was used:
Apparatus/Piece of Equipment Type/Producer
UPLC Aquity Series (pumps, autosampler, column manager), Waters, UK
Mass selective detector TripleQuad 5500, AB SCIEX, Germany
Multi-tube vortexer DVX-2500 Henry Troemner LLC, USA
Vortex mixer Vortex Genie 2; Scientific Industries, USA
Centrifuge Megafuge 1.0; Heraeus, Germany
Multipette(s), pipette(s) Eppendorf, Germany
Water bath SW21-C, Julabo, Germany Reagents For detecting C26 ceramide in a sample from a subject the following reagents were used. To that extent that values depend on temperature (e.g. the pH value) such values were determined at a temperature of 25° C.

Acetonitrile (ACN) HPLC-grade or Gradient

Acetone 99.5%

Dimethylsulfoxide (DMSO) HPLC grade

Ethanol (EtOH) p.a., 96%

Formic acid (FA) p.a., 98-100%

Methanol (MeOH) Gradient (LiChrosolv)

Trifluoroacetic acid (TFA) purum >98%

Water ASTM-I

The abbreviation "p.a." as used herein means "pro analysis".

The term "purum" as used herein, preferably means a commercial grade of a chemical compound having a purity of the above specified value.

ASTM-I as used herein refers to a water grade standard purity achieved by purification methods comprising Reverse Osmosis and Ultraviolet (UV) Oxidation.

Preparation of Calibration Standards

For calibration, all calibration standard C26 ceramide mentioned above having five concentration levels between 2.00 and 200 ng/mL were used.

Preparation of Internal Standard

The Internal Standard (IS 1) stock solution was prepared dissolving 25 µg of C25 ceramide (as delivered by Avanti) in DMSO/MeOH (1/1; vol/vol) to a concentration of 50 ng/mL.

Storing of Samples and Solutions

Control samples or study samples either were immediately stored below −20° C. Standard solutions as well as Internal Standard working solutions were stored between 2° C. and 8° C. until use.

Sample Preparation for Analysis 3 punches Ø of 3.2 µm were cut from the filtercard with dried blood spots and subjected to extraction in internal standard solution in DMSO: water: ethanol vol. 1:1:2 for 60 minutes at 37° C. and sonicated 20 minutes at 40° C. The solution containing internal standard and blood extract was transferred to a filter plate and then to a 96 well plate by centrifugation at 3.500 rpm.

Methods

A person skilled in the art will acknowledge that methods for detecting C26 ceramide in a sample from a subject using mass spectrometric analysis may also employ other transitions and fragments which allow for specific detection of and/or quantification of C26 ceramide in said sample from a subject.

Software

Data acquisition, data processing, statistics and calculations were performed using Analyst software 1.6.2 or higher (AB SCIEX, USA/Canada).

Example 2: Determining C26 Ceramide in DBS from Healthy Subjects and Farber's Disease Patients and Farber's Disease Carriers

TABLE 1

The samples used in this example were as follows:

| Sample description | Number of samples |
|---|---|
| Healthy controls fresh samples | 42 |
| Healthy controls 1 year old samples kept at RT | 5 |
| Healthy controls random samples | 59 |
| Farber's disease patients | 5 |
| Farber's disease carriers | 7 |

Figure 1:
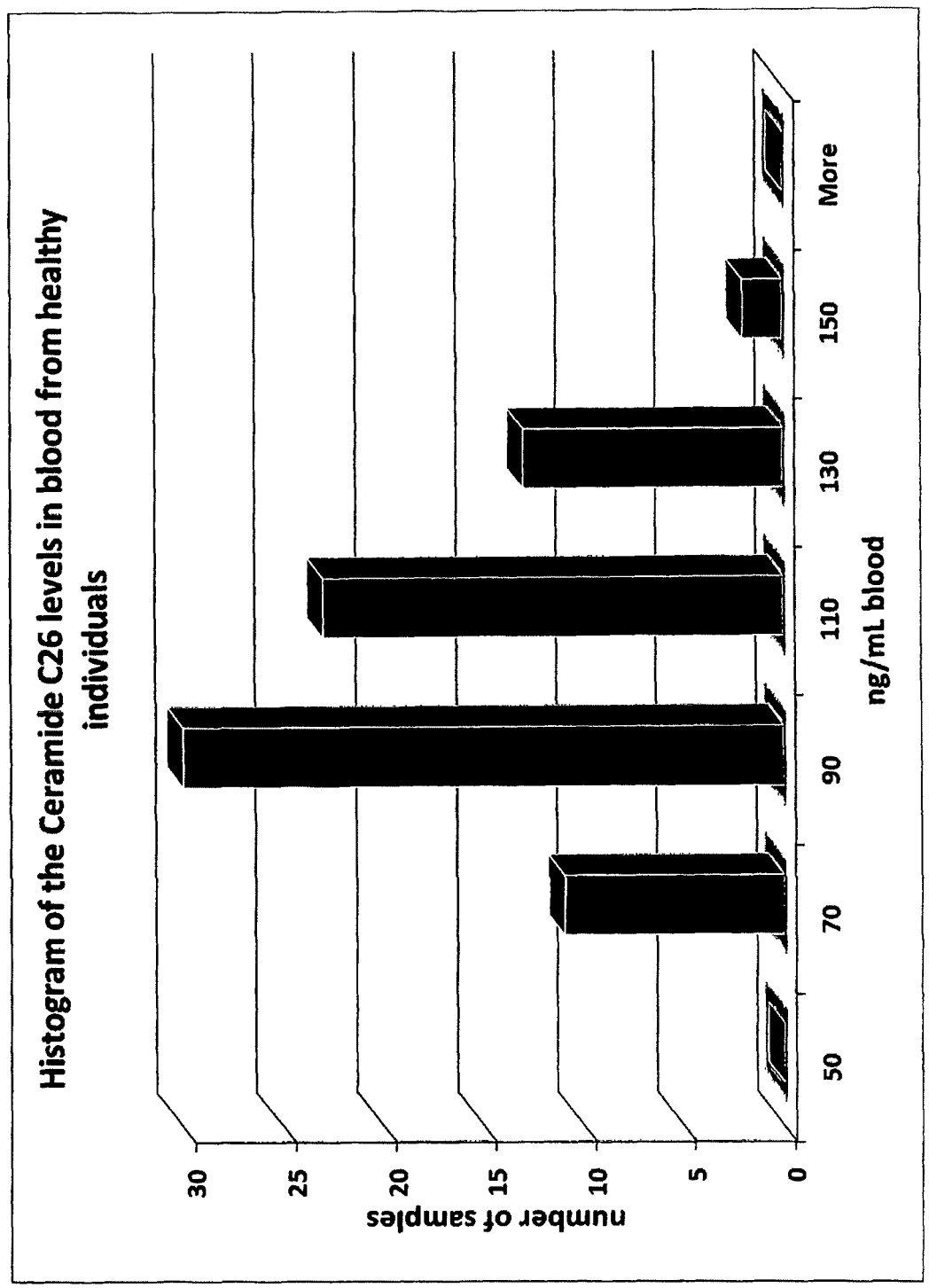
FIG. 1 is a histogram indicating levels of C26 ceramide in DBS of healthy subjects.

The following experiments were performed using the methods described at Example 1:
a) C26 ceramide level was determined in DBS from 79 random healthy controls. The results of the analyses are described in Table 2 and visualized in FIG. 1 showing a median level of 88.6 ng/mL.

TABLE 2

Results of the C26 ceramide determination in DBS from healthy controls Descriptive statistics

Figure 2:
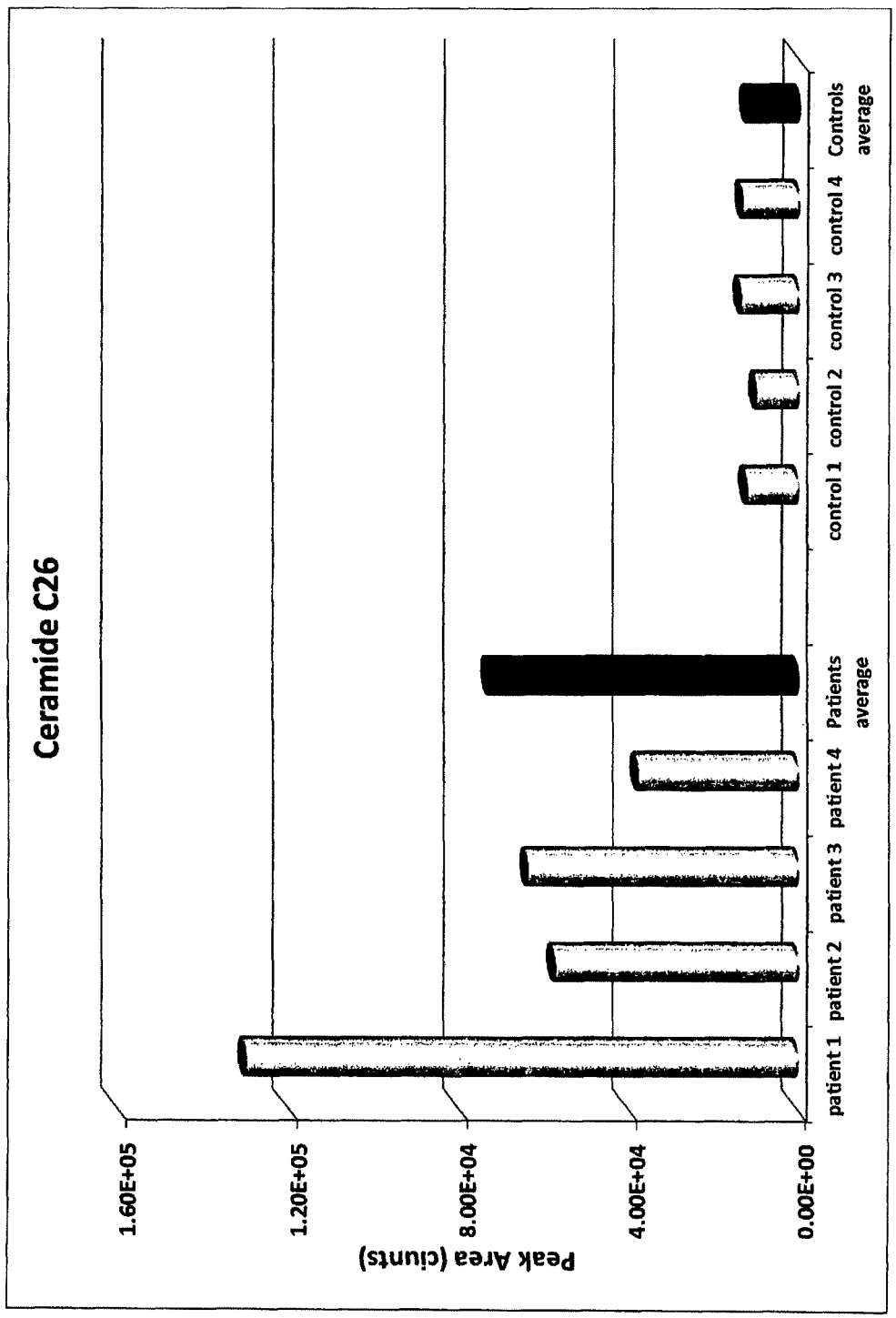
FIG. 2 is a diagram indicating signal of C26 ceramide expressed as peak area in DBS of 4 healthy subjects (the four columns on the left) vs. 4 Farber patients (the four columns on the right)
Figure 3:
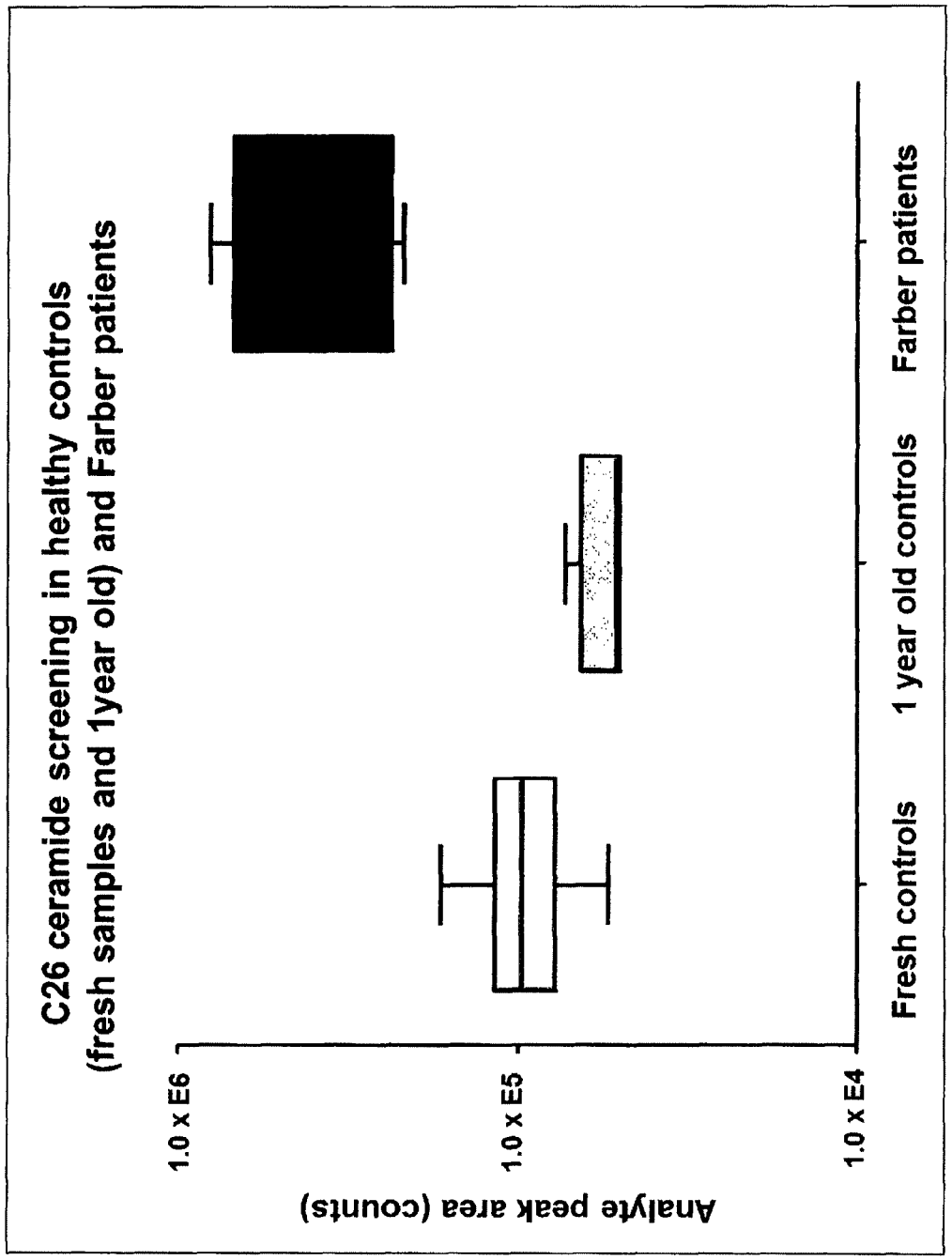
FIG. 3 is a diagram (whisker plot) indicating signal of C26 ceramide in DBS of 42 healthy subjects (fresh samples), 5 healthy subjects (1 year old samples) and 4 Farber patients.
Figure 4:
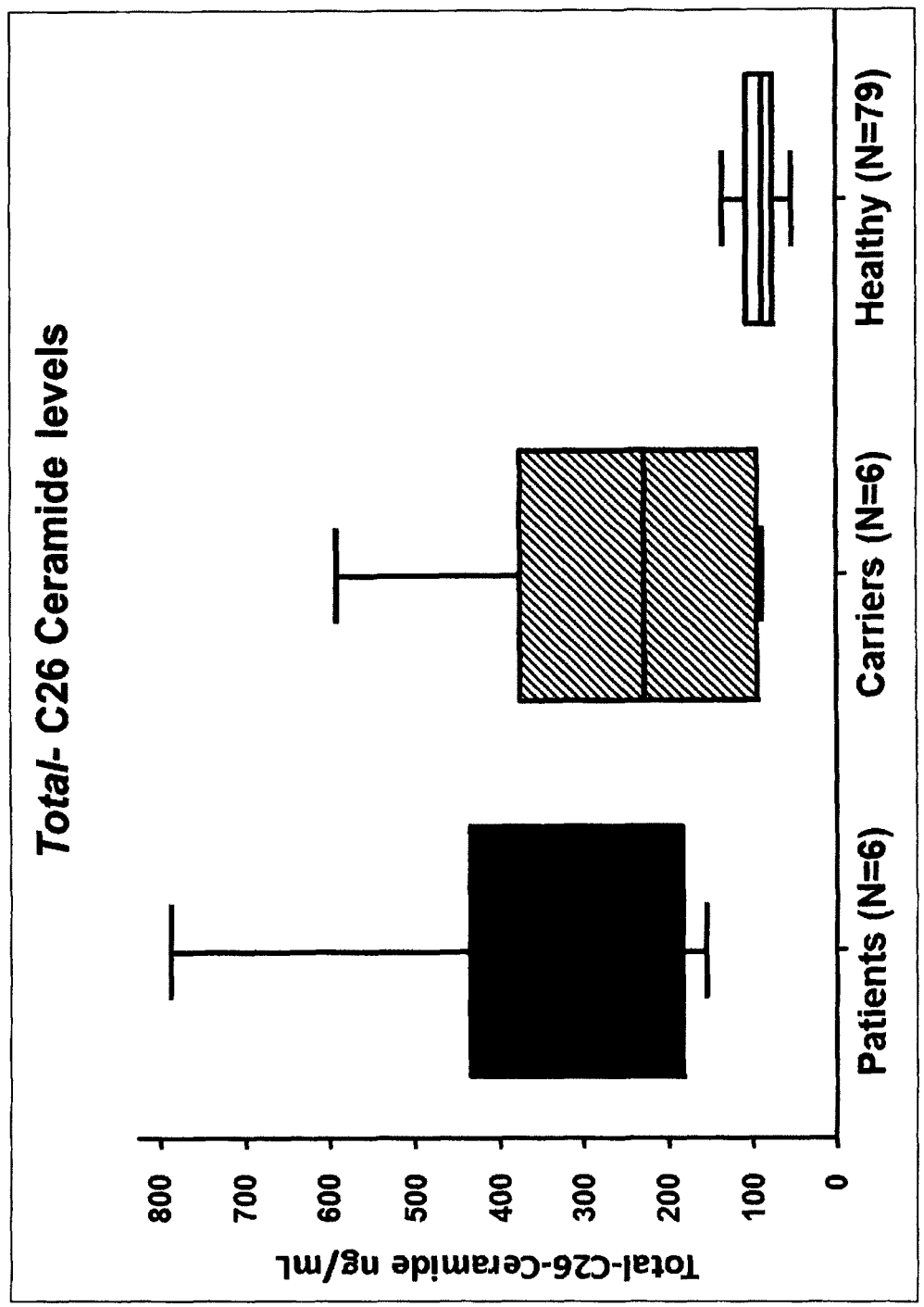
FIG. 4 is a diagram (whisker plot) indicating the level of total C26 ceramide in DBS of 6 Farber carriers, 6 Farber patients and 79 healthy subjects serving as controls, expressed in ng/ml.

| Mean | 90.9 |
|---|---|
| Standard Error | 2.2 |
| Median | 88.6 |
| Standard Deviation (STD) | 19.5 |
| Range | 81.9 |
| Minimum | 53.4 |
| Maximum | 135.3 |
| CUT OFF (Mean + 2 * STD) | 129.8 |
| Count | 79.0 | b) C26 ceramide signal was measured in DBS from 4 random healthy controls and 4 Farber's disease patients. The results of the analyses are visualized in FIG. 2. showing that the individual and average C26 levels in Farber' disease patients are higher compared with the levels found in healthy controls.
c) C26 ceramide signal was measured in DBS from 42 freshly collected samples from healthy controls, 5 old samples from healthy controls and 4 Farber's disease patients. The results of the analyses are visualized in FIG. 3. showing that C26 levels healthy controls are lower than the levels found in Farber's disease patients, irrespectively if the samples are fresh or have been stored.
d) C26 ceramide levels were determined in DBS from 79 healthy controls, 6 Farber's disease carriers and 6 Farber's disease patients. The results of the analyses are visualized in FIG. 4. and listed in Table 3. The results show a good separation between Farber's disease patients/carriers on the one hand and healthy controls on the other hand.

TABLE 3

|  | Farber's disease carriers | Farber's disease patients | Healthy controls |
|---|---|---|---|
| Number of samples | 6 | 6 | 79 |
| Minimum | 88.3 | 155.5 | 53.4 |
| 25% Percentile | 94.73 | 183.0 | 75.2 |
| Median | 228.1 | 247.7 | 88.6 |
| 75% Percentile | 375.0 | 433.6 | 106.7 |
| Maximum | 590.6 | 787.5 | 135.3 |
| Mean | 255.9 | 324.4 | 90.1 |

TABLE 3-continued

|  | Farber's disease carriers | Farber's disease patients | Healthy controls |
|---|---|---|---|
| Std. Deviation | 185.2 | 234.5 | 19.5 |
| Std. Error | 75.6 | 95.75 | 2.1 |

Example 3: Determining Cis-C26 Ceramide and Trans-C26 Ceramide in DBS from Healthy Subjects and Farber's Disease Patients and Farber's Disease Carriers The levels of Ceramide C26 isomers were tested in 6 genetically confirmed Farber patients, 6 genetically confirmed Farber carriers and 79 normal controls. In the experiments a standard curve with Ceramide C26 was used and the results were expressed in ng/mL of blood. The results are summarized in the table 4.

TABLE 4

|  | Farber patients (N = 6) | | | Farber Carriers (N = 6) | | | Healthy controls (n = 79) | | |
|---|---|---|---|---|---|---|---|---|---|
|  | Total C26 | Trans C26 | Cis C26 | Total C26 | Trans C26 | Cis C26 | Total C26 | Trans C26 | Cis C26 |
| mean | 324 | 18 | 307 | 256 | 28 | 228 | 91 | 29 | 62 |
| maximum | 788 | 20 | 768 | 591 | 45 | 571 | 135 | 44 | 103 |
| minimum | 155 | 11 | 139 | 88 | 20 | 43 | 53 | 18 | 134 |
| Standard deviation |  |  |  |  |  |  | 19 | 6 | 18 |
| Cut-off |  |  |  |  |  |  | 130 | 41 | 97 |

Figure 5:
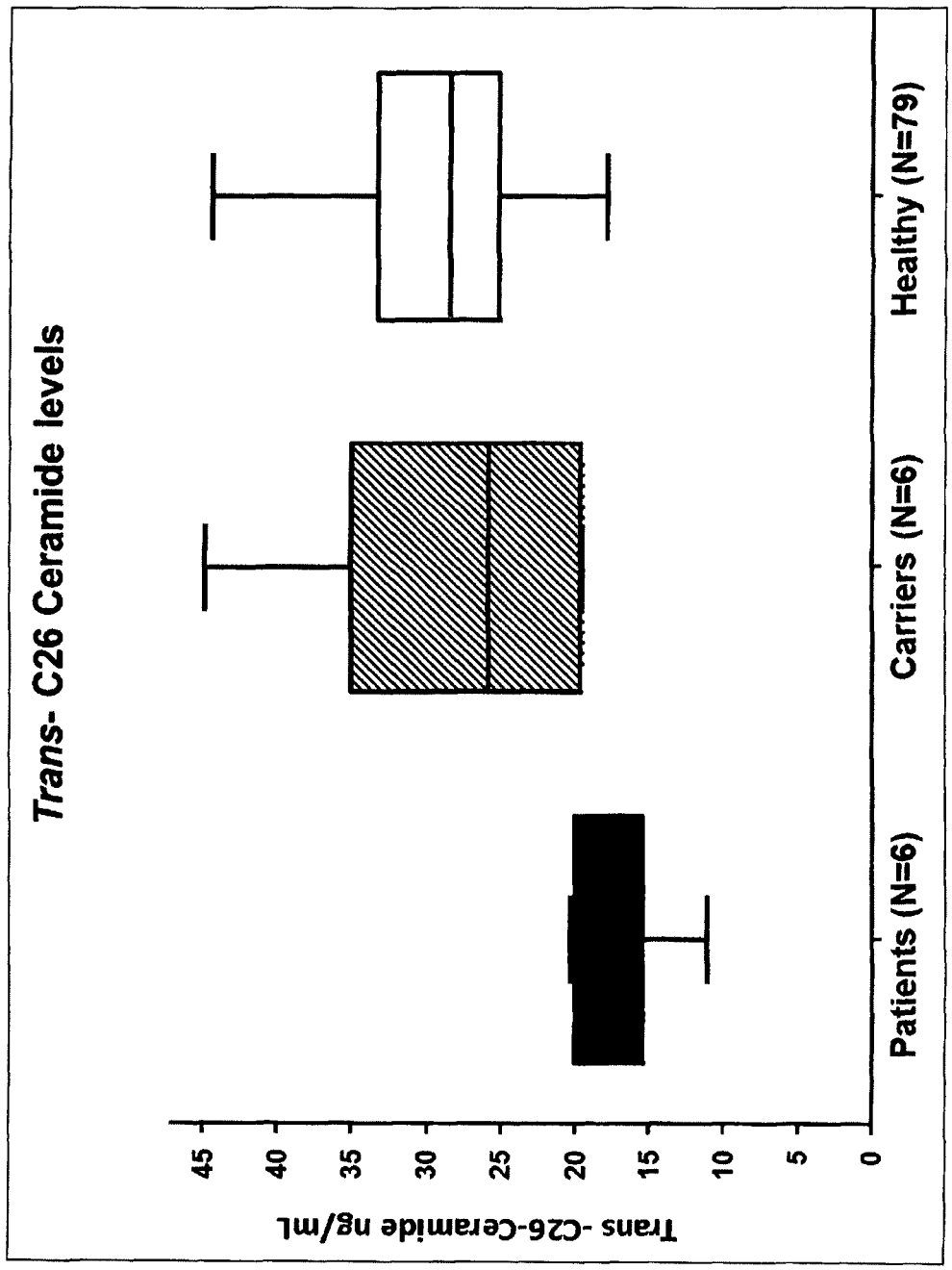
FIG. 5 is a diagram (whisker plot) indicating the level of cis C26 ceramide in DBS of 6 Farber carriers, 6 Farber patients and 79 healthy subjects serving as controls, expressed in ng/ml.
Figure 6:
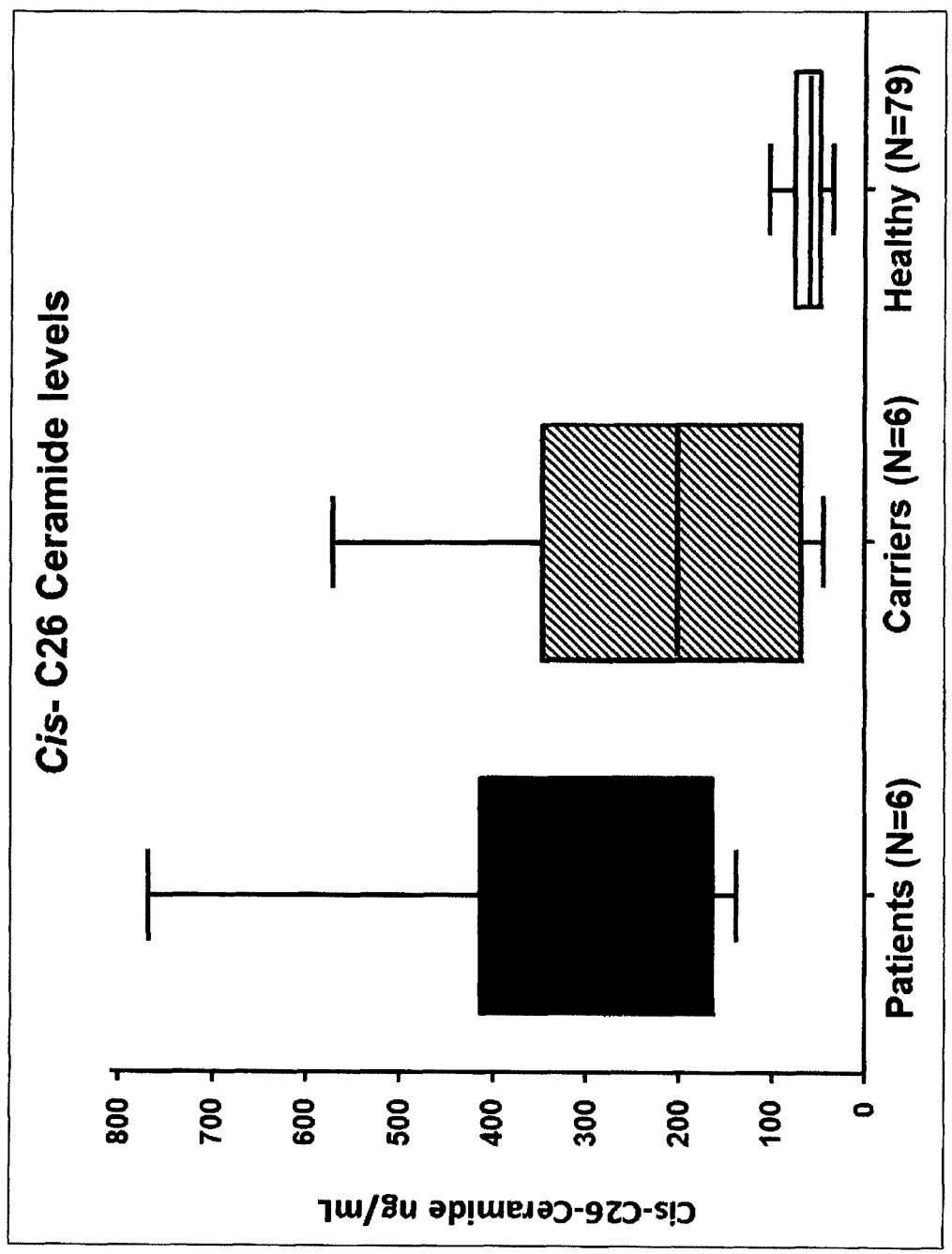
FIG. 6 is a diagram (whisker plot) indicating the level of trans C26 ceramide in DBS of 6 Farber carriers, 6 Farber patients and 79 healthy subjects serving as controls, expressed in ng/ml.

The results are also illustrated in FIGS. 5 and 6.

The experiments show that the cis-isomer rather than the trans-isomer of C26 ceramide is mainly accumulating in the lysosomes of Farber patients. Cis-C26 ceramide and total C26 ceramide can be used as biomarkers for Farber disease to distinguish between healthy persons and Farber patients. Trans-C26 ceramide levels are slightly decreased in patient samples.

Example 4: Standardization and Validation of Cis-C26 Ceramide and Trans-C26 Ceramide Assay The normal range of C26 ceramides levels in blood was determined on a group of 192 normal controls with ages from 3 months to 65 years. The results show that total C26—ceramide has a value of 49.8±9.6 nmol/L blood, from which 18.5±4.9 nmol/L is isoform 1 blood and 33.8±8.6 nmol/L isoform 2. For the pathological range, 10 clinically confirmed Farber patients with ages from 2 months to 22 years were found to have a total C26 ceramide concentration of 134.8±52.2 nmol/L blood, from which 94.6±55.4 nmol/L blood is isoform 1 (which is cis-C26 ceramide) and 40.1±19.6 nmol/L isoform 2 (which is trans-C26 ceramide).

The cut-off for total C26—ceramide was set at 69.0 nmol/L and at 28.3 nmol/L for isoform 1 (mean value of the normal controls+2*standard deviation).

Figure 7:
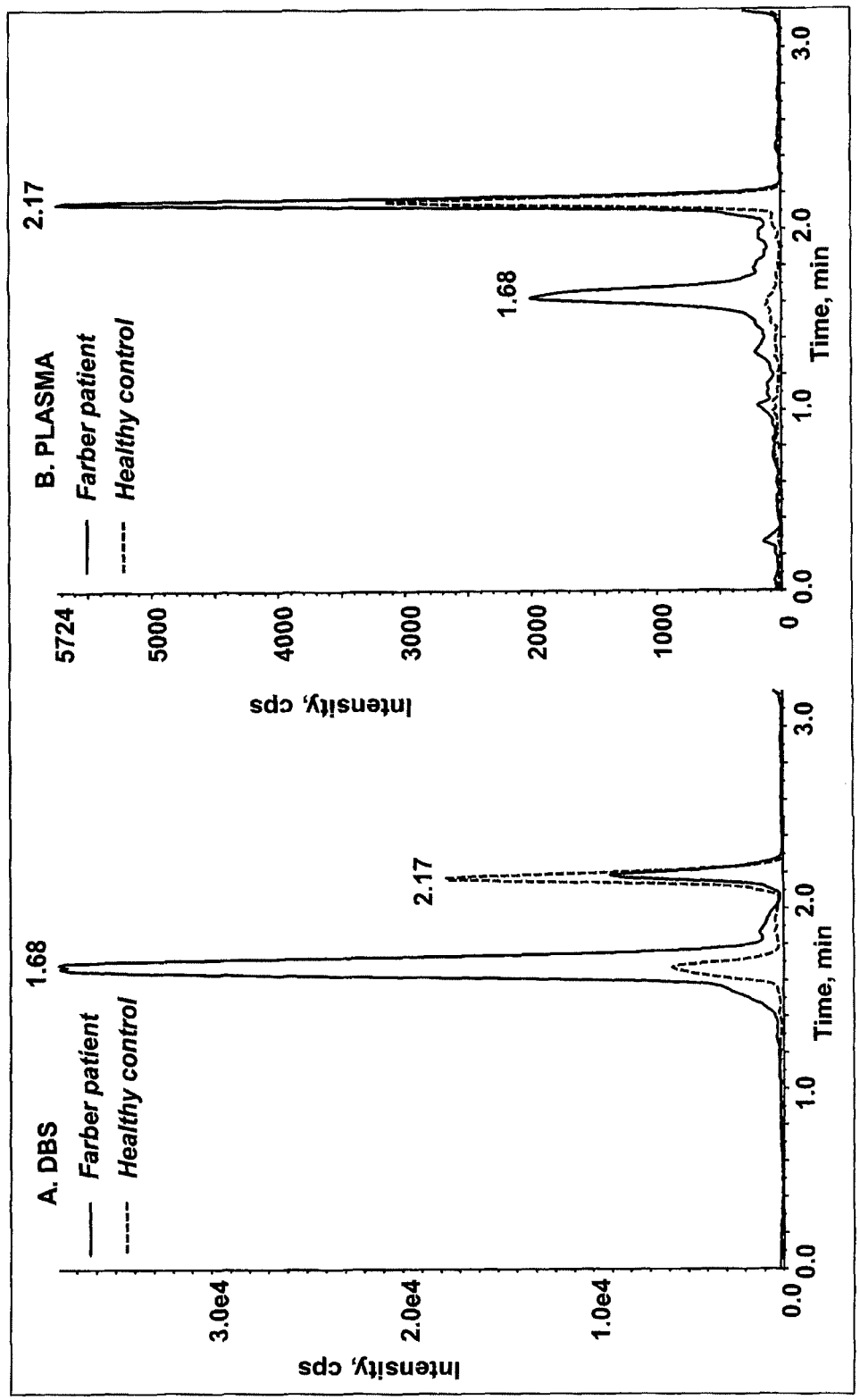
FIG. 7 is a panel of diagrams showing the level of cis-C26 ceramide (isoform 1) as nmol/L blood sample, trans-C26 ceramide (isoform 2) as nmol/L sample, the ratio of both isoforms and the level of total C26 ceramide as nmol/L blood sample for newborns, for juveniles and adults being subjects suffering from Farber's disease (FP), subjects being Farber carriers (FC) or normal controls (NC)

When the results of C26 ceramide analyses are grouped according to the patients ages into newborns (up to 6 months, Farber phenotype); juveniles (6 months to 17 years, Farber phenotype) and adults (>17 years, SMA phenotype), several trends emerge: (i.) the concentration ranges of C26 ceramide and its isoforms in normal controls are not changing with age; (ii.) isoform 1 is extremely high in the newborn Farber patients (187.5±6.4 nmol/L) and decreases in juvenile (80.8±27.1 nmol/L) and even more in the patients that reach adulthood (though still above the normal range, 43.0±12.7 nmol/L); (iii.) isoform 2 is in normal range in newborn Farber patients (31.0±2.0 nmol/L) and increases to pathological levels in patients that reach adulthood (72.0±21.2 nmol/L); (iv.) both isoform 1 and isoform 2 are low (in normal range) in the newborn Farber carriers and could increase in time to pathological levels although the carriers included in this study do not present clinical symptoms characteristic to FD; moreover the levels in adult carriers seem to decrease compared with the juvenile carriers. The results are also illustrated in FIG. 7 Said FIG. 7 shows C26 ceramide levels in the blood of Farber patients referred to as FP, Farber carriers referred to as FC and normal controls referred to as NC. All the patients, carriers and normal controls were grouped according to the donors ages in newborns (up to 6 months), juveniles (6 months to 17 years) and adults (>17 years).

assay) in two different batches (inter-assay). The coefficient of variation (CV %) for within-run precision was found to be between 3.1% and 4.2% and between-runs 3.7% and 6.1%. Accuracy of the quantification method was investigated using 7 solutions of trans-C26 ceramide of different concentrations, covering different areas of the calibration line (low, medium, high and above the highest point in the calibration line) 6 times on the same batch in 2 different batches. For accuracy, within-run CV % was found to be between 1.7 to 3.8% and between-runs 0.3-2.7%. Linearity of the standard curve was determined 5 times in the same batch using 7 solutions of trans-C26 ceramide of different concentrations (0 ng/mL to 100 ng/mL).

The curve was found to be linear with R values between 0.9981 and 0.9996. The selectivity of the measurement was insured by using LC-MRM-MS, cross-contamination was checked for each batch by injecting IS solution after the highest concentration of the standard curve. Limit of detection was found to be 0.12 ng/mL and limit of quantification 0.4 ng/mL in blank filter paper. Robustness of the method was checked by measurement of the DBS extract immediately after the sample preparation, at 12 h after the sample preparation and at 24 h after the sample preparation. Total C26 ceramide and isoform 1 were increased above cutoff for all the investigated Farber samples, for this cohort (100% sensitivity).

TABLE 5

Concentration of C26 ceramide isoforms in the blood of Farber patients, Farber carriers and normal controls.

| Samples | N | Ceramide C26:0 (nmol/L) (mean ± STD) | | | |
|---|---|---|---|---|---|
| | | Isoform1 | Isoform2 | ratio | Total |
| Farber Patients | | | | | |
| Newborns (0-6 months) | 2 | 187.5 ± 6.4 | 31.0 ± 2.0 | 6.1 ± 0.2 | 218.5 ± 9.1 |
| Juvenile (0.5-17 years) | 6 | 80.8 ± 27.1 | 32.5 ± 9.4 | 2.6 ± 1.0 | 113.5 ± 34.05 |
| Adults (>17 years) | 2 | 43.0 ± 12.7 | 72.0 ± 21.2 | 0.6 | 115.0 ± 33.9 |
| All Farber patients | 10 | 94.6 ± 55.4 | 40.1 ± 19.6 | 2.9 ± 2.0 | 134.8 ± 52.2 |
| Farber Carriers | | | | | |
| Newborns (0-6 months) | 1 | 34.0 | 28.0 | 1.2 | 62.0 |
| Juvenile (0.5-17 years) | 2 | 193.0 ± 36.0 | 53.0 ± 33.9 | 4.3 ± 2.1 | 246.5 ± 71.4 |
| Adults (>17 years) | 8 | 59.63 ± 31.89 | 40.4 ± 13.0 | 1.6 ± 0.7 | 99.9 ± 34.1 |
| All Farber carriers | 11 | 81.6 ± 62.8 | 41.6 ± 16.7 | 2.0 ± 1.4 | 123.1 ± 71.92 |
| Normal Controls | | | | | |
| Newborns (0-6 months) | 31 | 18.3 ± 5.8 | 35.3 ± 11.8 | 0.6 ± 0.3 | 53.6 ± 11.7 |
| Juvenile (0.5-17 years) | 78 | 19.7 ± 5.1 | 25.9 ± 10.43 | 0.6 ± 0.2 | 50.5 ± 10.7 |
| Adults (>17 years) | 83 | 17.4 ± 4.1 | 31.5 ± 6.5 | 0.6 ± 0.2 | 48.6 ± 8.1 |
| All normal controls | 192 | 18.5 ± 4.9 | 33.8 ± 8.6 | 0.6 ± 0.2 | 49.8 ± 9.6 |
| Cut-off (mean$_{controls}$ + 2 * STD) | | 28.3 | — | — | 69.0 |

These results indicate that in classical Farber phenotype isoform 1 is dominant from the first months of life while for SMA phenotype isoform 2 is accumulating dominantly. Nevertheless the concentration of the total C26 ceramide and the concentration of isoform 1 can be used as specific biomarkers to clearly distinguish between the normal controls and Farber patients.

Characteristics of the C26 Ceramide Assay for Farber Disease Diagnosis

Precision of the assay was checked by determining the C26 ceramides levels in one Farber sample and in one normal control sample 6 times in the same batch (intra- The specificity of the total C26 ceramide and isoform 1 as biomarkers for Farber, C26 Ceramide content was investigated using the 10 Farber patients, 192 normal controls, 2 JIA (juvenile idiopathic arthritis) patients and 30 genetically confirmed LSD patients (5 GD (Gaucher disease), 5 PD (Pompe disease), 5 NPA/B (Niemann-Pick type A/B, 5 FD and 5 MPS 2 (mucopolysaccharidosis type 2). The results show that the two biomarkers are increased above the cutoff for the Farber patients and below the cut-off for all the normal controls, JIA patients and patients affected by LSDs characterized by an impaired enzyme.

TABLE 6

Concentration of C26 ceramide isoforms in the blood of Farber patients, JIA patients, patients affected by other LSD and normal controls.

| Samples | N | Ceramide C26:0 (nmol/L) | | | |
|---|---|---|---|---|---|
| | | Isoform1 | Isoform2 | Ratio | Total |
| Cut-off | | 28.3 | — | — | 69.0 |
| Farber's Patients | 10 | 94.6 ± 55.4 | 40.1 ± 19.6 | 2.9 ± 2.0 | 134.8 ± 52.2 |
| Juvenile idiopathic arthritis Patients | 2 | 17.5 ± 0.7 | 37.5 ± 14.8 | 0.5 ± 0.3 | 55.0 ± 14.1 |
| Gaucher Patients | 5 | 24.0 ± 1.4 | 35.6 ± 6.8 | 0.7 ± 0.2 | 59.3 ± 6.8 |
| Pompe Patients | 5 | 21.3 ± 3.0 | 28.8 ± 2.3 | 0.8 ± 0.1 | 50.0 ± 5.0 |
| Niemann-Pick Type A/B Patients | 5 | 19.5 ± 7.8 | 28.5 ± 9.9 | 0.8 ± 0.3 | 48.5 ± 13.3 |
| Fabry Patients | 5 | 25.5 ± 3.8 | 32.5 ± 1.0 | 0.8 ± 0.2 | 57.5 ± 3.0 |
| Hunter Patients | 5 | 23.3 ± 5.6 | 35.8 ± 7.0 | 0.7 ± 0.1 | 59.0 ± 10.8 |
| All Normal Controls | 192 | 18.5 ± 4.9 | 33.8 ± 8.6 | 0.6 ± 0.2 | 49.8 ± 9.6 |

Example 5: Confirmation of the C26 Ceramide Structure as Biomarker for Farber's Disease Further MS/MS analyses confirmed the presence of the same compound in both peaks corresponding to the C26 Ceramide transition. The two peaks correspond to the cis- and trans-isomers of the C26 ceramide. This is based on the fact that pure trans-C26 ceramide has the same retention time (2.17 min) and fragmentation pattern as the Isoform 2 found in biological samples (see FIG. 8 and FIG. 9).

More specifically, FIG. 8 shows the total ion chromatogram (TIC) profile of C26-ceramide isoforms in samples from genetically confirmed Farber patients vs normal controls, whereby the isoforms were analyzed from were dried blood spots (A) or from in clear plasma (B) (clear plasma was prepared from whole blood with no visible signs of hemloysis. In DBS both isoforms are present in both samples from healthy controls and Farber patients; while the isoform 1 is dominant in the Farber patients samples, the isoform 2 is dominant in healthy controls. Isoform 1 is not present in the samples from healthy controls, while in the samples of Farber patients it can be quantified.

More specifically, FIG. 9. shows the fragmentation patterns of the two isoforms of Ceramide C26 separable by LC/MS which are the cis- and trans-isomers of the C26. This is based on two facts: (i.) the analysis of pure trans-C26 ceramide reveals that it elutes at RT 2.17 min (second peak) and (ii.) the fragmentation pattern is identical for the two peaks.

The features of the present invention disclosed in the specification, the claims, the sequence listing and/or the drawings may both separately and in any combination thereof be material for realizing the invention in various forms thereof.

The invention claimed is:

1. A method for diagnosing Farber's disease in a subject, wherein the method comprises the following steps:
   i) adding an internal standard to a sample from the subject, wherein the sample from the subject is selected from the group comprising plasma, serum and blood;
   ii) optionally mixing the sample containing the internal standard;
   iii) subjecting the sample to a protein precipitation and/or a biomarker extraction step, whereby protein from the sample is precipitated and/or the biomarker is extracted and a first supernatant of the sample is provided;
   iv) optionally subjecting the first supernatant of the sample or at least a part thereof to a first separation step which provides a second supernatant, whereby the first separation step is a step of centrifugation;
   v) subjecting the first supernatant and/or the second supernatant, or at least a part thereof, to a second separation step, wherein the second separation step comprises injecting at least a part of the first supernatant and/or at least a part of the second supernatant into an HPLC-MS/MS system and using an HPLC column with a gradient from acidic water to acetonitrile/acetone; wherein the HPLC column is preferably an HPLC column selected from the group consisting of a C8 HPLC column and a C18 HPLC column, and wherein the second separation step provides a separated sample; and
   vi) subjecting the separated sample to mass spectrometry analysis, wherein mass spectrometry comprises electrospray ionization multiple reacting monitoring (ESI-MRM MS),
   wherein the mass spectrometry analysis comprises
   a step a), wherein the step a) comprises detecting a biomarker in the separated sample from the subject, and optionally
   a step b), wherein the step b) comprises determining a level of the biomarker present in the separated sample,
   wherein the level of the biomarker is indicative of whether or not the subject is suffering from Farber's disease or whether or not the subject is at risk of suffering from Farber's disease, and
   wherein the biomarker is C26 ceramide.

2. The method of claim 1, wherein the internal standard is selected from the group consisting of N-lauroyl sphingosine, lyso-Gb2, a C17 ceramide, a C19 ceramide, a C21 ceramide, a C23 ceramide and a C25 ceramide, deuterated C26 ceramide.

3. A method for the treatment of a subject suffering from or being at risk of developing Farber's disease, wherein the method comprises
   a) performing an assay to detect a biomarker in a sample from the subject;
   b) determining a level of the biomarker present in the sample;
   c) comparing the level of the biomarker present in the sample to a cut-off value; and
   d) treating the subject with a therapy selected from the group consisting of administration of a corticosteroid to the subject, enzyme replacement therapy and bone marrow transplantation if the level of the biomarker present in the sample is higher than the cut-off value, wherein the biomarker is C26 ceramide.

4. The method according to claim 1, wherein the subject is a human.

* * * * *